United States Patent [19]

Bru-Magniez et al.

[11] Patent Number: 5,387,747

[45] Date of Patent: * Feb. 7, 1995

[54] TRIAZOLOPYRIMIDINE DERIVATIVES WHICH ARE ANGIOTENSIN II RECEPTOR ANTAGONISTS, THEIR METHODS OF PREPARATION AND PHARMACEUTICAL COMPOSITIONS IN WHICH THEY ARE PRESENT

[75] Inventors: Nicole Bru-Magniez, Paris; Timur Güngor, Rueil Malmaison; Jean-Marie Teulon, La Celle Saint Cloud, all of France

[73] Assignee: Laboratoires Upsa, Agen, France

[ * ] Notice: The portion of the term of this patent subsequent to May 31, 2011 has been disclaimed.

[21] Appl. No.: 39,382

[22] PCT Filed: Feb. 18, 1993

[86] PCT No.: PCT/FR93/00161

§ 371 Date: Apr. 16, 1993

§ 102(e) Date: Apr. 16, 1993

[87] PCT Pub. No.: WO93/17024

PCT Pub. Date: Sep. 2, 1993

Related U.S. Application Data

[63] Continuation-in-part of Ser. No. 863,955, Apr. 6, 1992, Pat. No. 5,231,094.

[30] Foreign Application Priority Data

Feb. 24, 1992 [FR] France .................................. 92 02109
Apr. 30, 1992 [FR] France .................................. 92 05417

[51] Int. Cl.$^6$ ............................................ C07D 487/04
[52] U.S. Cl. ...................... 514/233.2; 514/253; 514/258; 544/118; 544/263; 548/239; 546/286; 546/318; 558/411; 549/61; 549/474
[58] Field of Search ................... 544/263, 118; 514/233.2, 258, 253

[56] References Cited

U.S. PATENT DOCUMENTS

| | | | |
|---|---|---|---|
| 5,177,074 | 1/1993 | Allen et al. | 544/118 |
| 5,217,973 | 6/1993 | Brumagniez et al. | 544/263 |
| 5,231,094 | 7/1993 | Brumagniez et al. | 544/263 |
| 5,250,521 | 10/1993 | Allen et al. | 514/258 |

FOREIGN PATENT DOCUMENTS

WO91-15209  10/1991  WIPO.

*Primary Examiner*—Donald G. Daus
*Attorney, Agent, or Firm*—Rosen, Dainow & Jacobs

[57] ABSTRACT

The present invention relates to the derivatives of the formula

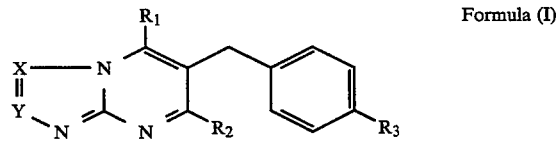

Formula (I)

and their tautomeric forms, as well as their addition salts, and to their use in therapeutics, especially for the treatment and prevention of cardiovascular diseases and in particular for the treatment of hypertension, cardiac insufficiency and diseases of the arterial wall, especially atherosclerosis.

11 Claims, No Drawings

TRIAZOLOPYRIMIDINE DERIVATIVES WHICH ARE ANGIOTENSIN II RECEPTOR ANTAGONISTS, THEIR METHODS OF PREPARATION AND PHARMACEUTICAL COMPOSITIONS IN WHICH THEY ARE PRESENT

This application is a continuation-in-part of U.S. Ser. No. 07/863,995 filed Apr. 6, 1992, now U.S. Pat. No. 5,231,094.

The present invention relates, by way of novel products, to the triazolopyrimidine derivatives of general formula (I) below and their tautomeric forms and, where appropriate, their addition salts, in particular the pharmaceutically acceptable addition salts.

The compounds in question have a very valuable pharmacological profile insofar as they possess antagonistic properties towards the angiotensin II receptors, and antiproliferative properties. They are therefore particularly indicated for the treatment and prevention of cardiovascular diseases and in particular for the treatment of hypertension, for the treatment of cardiac insufficiency and for the treatment and prevention of diseases of the arterial wall, especially atherosclerosis.

The present invention further relates to the method of preparing said products and to their uses in therapeutics.

These triazolopyrimidine derivatives and their tautomeric forms have general formula (I):

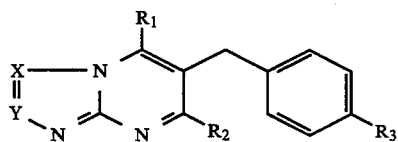

Formula (I)

In formula (I):
one of the radicals $R_1$ and $R_2$ is
  a lower alkyl radical having 1 to 6 carbon atoms;
  an ether radical of the formula $-(CH_2)_pOR$, in which p is an integer from 1 to 6 and R is a lower alkyl radical having 1 to 6 carbon atoms or a benzyl radical; or
  an alcohol radical of the formula $-(CH_2)_pOH$, in which p is as defined above; and
the other radical $R_1$ or $R_2$ is
  the hydrogen atom;
  a halogen atom;
  a lower alkyl radical having 1 to 6 carbon atoms; or
  a radical selected from the group comprising the radicals $N_3$, $OR_4$, $SR_4$, $NR_5R_6$ and $NH(CH_2)_n$-$NR_5R_6$, in which:
$R_4$ is
  the hydrogen atom;
  a lower alkyl radical having 1 to 6 carbon atoms or a $C_3$–$C_7$ cycloalkyl radical;
  a radical $(CH_2)_m$-$COOR'$, m being an integer from 1 to 4 and R' being the hydrogen atom or a lower alkyl radical having 1 to 6 carbon atoms; or
  a radical $(CH_2)_m$-O-R', m and R' being as defined above;
$R_5$ and $R_6$, which are identical or different, are
  the hydrogen atom; or
  a lower alkyl radical having 1 to 6 carbon atoms or a $C_3$–$C_7$-cycloalkyl radical; or
$R_5$ and $R_6$, taken together with the nitrogen atom to which they are attached, form a heterocycle selected from morpholine, pyrrolidine or piperidine; and
n is an integer from 1 to 4;
X and Y, which are different, are
  in one case the nitrogen atom; and
  in the other case a group C-$R_7$, in which $R_7$ is
    the hydrogen atom;
    a lower alkyl radical having 1 to 6 carbon atoms or a $C_3$–$C_7$-cycloalkyl radical;
    a radical $(CH_2)_{n'}OH$, in which n' is an integer from 0 to 4;
    a radical SR', R' being as defined above; or
    a radical $NR_5R_6$, in which $R_5$ and $R_6$, which are identical or different, are the hydrogen atom, a lower alkyl radical having 1 to 6 carbon atoms or a $C_3$–$C_7$-cycloalkyl radical; and
$R_3$ is a radical of the formula

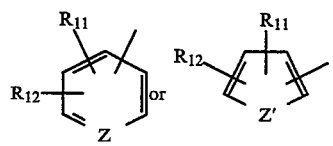

in which:
Z is CH or N or Z' is S or O;
$R_{11}$ is the hydrogen atom or a halogen atom; and
$R_{12}$ is a tetrazole radical, CN, COOH or $CONH_2$.

The above-mentioned derivatives must also be considered in their tautomeric form.

In the case where $R_2$ is an azide group, the compounds may be considered in the tricyclic tetrazolo-[1,5-c]-1,2,4-triazolo[1,5-a]pyrimidine form according to the equilibrium well known in the literature (cf. Temple and Montgomery, J. Org. Chem., 30, 826 (1965)).

The above-mentioned derivatives can take the form of addition salts, in particular the pharmaceutically acceptable addition salts.

Advantageously, the derivatives of the invention have general formula (I) given above in which:
one of the radicals $R_1$ and $R_2$ is
  a lower alkyl radical having 1 to 6 carbon atoms;
  an ether radical of the formula $-(CH_2)_pOR$, in which p is an integer from 1 to 6 and R is a lower alkyl radical having 1 to 6 carbon atoms or a benzyl radical; or
  an alcohol radical of the formula $-(CH_2)_pOH$, in which p is as defined above; and
the other radical $R_1$ or $R_2$ is
  the hydrogen atom;
  a halogen atom;
  a lower alkyl radical having 1 to 6 carbon atoms; or
  a radical selected from the group comprising the radicals $N_3$, $OR_4$, $SR_4$, $NR_5R_6$ and $NH(CH_2)_n$—$NR_5R_6$, in which:
$R_4$ is
  the hydrogen atom; or
  a radical $-(CH_2)_m$—O—R' in which m is an integer from 1 to 4 and R' is a lower alkyl radical having 1 to 6 carbon atoms;
$R_5$ and $R_6$, which are identical or different, are
  the hydrogen atom; or
  a lower alkyl radical having 1 to 6 carbon atoms; or
$R_5$ and $R_6$, taken together with the nitrogen atom to which they are attached, form a heterocycle selected from morpholine, pyrrolidine or piperidine; and n is an integer from 1 to 4;

X and Y, which are different, are in one case the nitrogen atom; and in the other case a group C—R₇ in which R₇ is the hydrogen atom;
a lower alkyl radical having 1 to 6 carbon atoms;
a radical (CH₂)ₙ'OH, in which n' is an integer from 0 to 4;
a radical SR', R' being as defined above; or
a radical NR₅R₆ in which R₅ and R₆, which are identical or different, are the hydrogen atom or a lower alkyl radical having 1 to 6 carbon atoms; and R₃ is one of the following radicals:

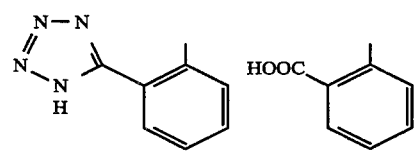

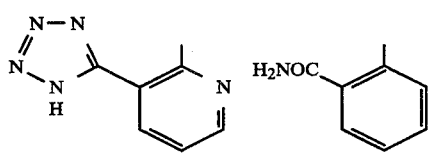

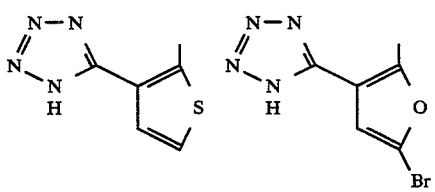

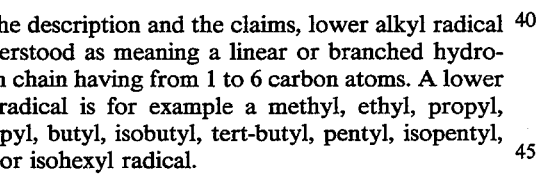

In the description and the claims, lower alkyl radical is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

C₃-C₇-Cycloalkyl radical is understood as meaning a saturated cyclic hydrocarbon radical, preferably a cyclopropyl, cyclobutyl, cyclohexyl or cycloheptyl radical.

Halogen is understood as meaning a chlorine, bromine, iodine or fluorine atom.

In one embodiment, R₁ is an n-propyl group.

In another embodiment, R₁ is an N-diethylamino group.

In another embodiment, R₁ is an n-butyl group.

In one embodiment, R₂ is a hydroxyl group.

In another embodiment, R₂ is an n-propyl group.

In another embodiment, R₂ is an N-diethylamino group.

In one embodiment, R₃ is a 2-(1H-tetrazol-5yl)phenyl group.

In one embodiment, X is the nitrogen atom.

In one embodiment, Y is the group CH.

In another embodiment, Y is the group C—CH₃.

In another embodiment, Y is the group C—NH₂.

The particularly preferred compounds of the invention are selected from the products of the formulae

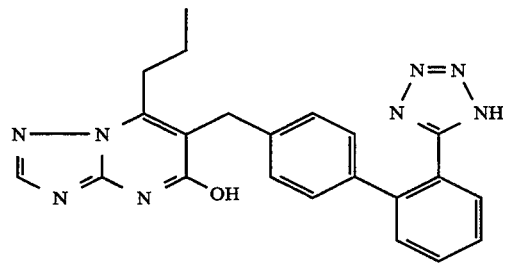

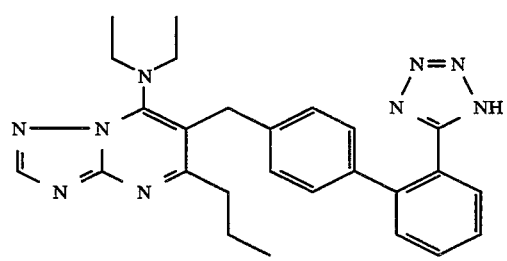

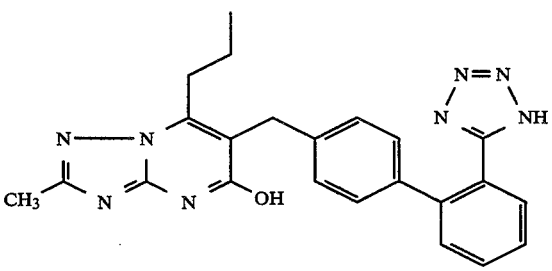

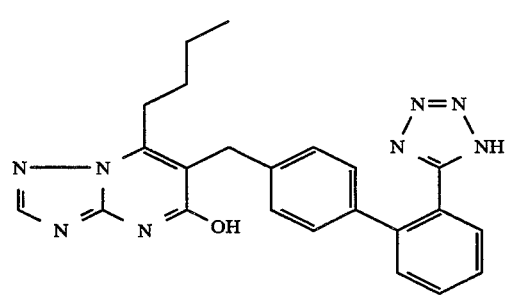

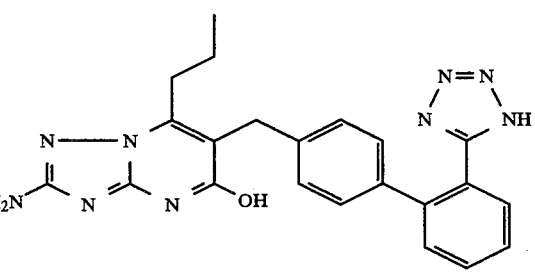

-continued

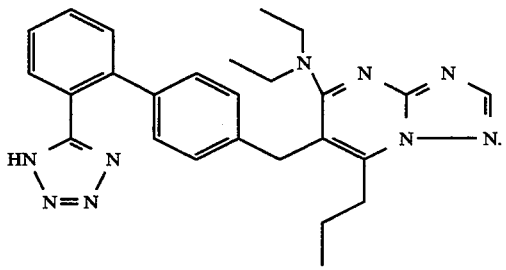

In general terms, the method of preparing the compounds of formula (I) comprises:

a) preparing a compound of formula (α):

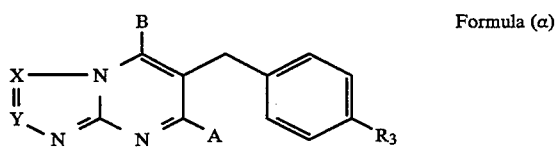

Formula (α)

in which:

X, Y and R₃ are as defined above; and

A and B are in one case a hydroxyl group or a lower alkyl radical having 1 to 6 carbon atoms and in the other case a lower alkyl radical having 1 to 6 carbon atoms or an ether radical of the formula —(CH$_2$)$_p$—OR, in which p is an integer from 1 to 6 and R is a lower alkyl radical having 1 to 6 carbon atoms or a benzyl radical, by condensing a 3-amino-1,2,4-triazole of formula (II):

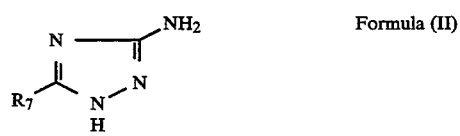

Formula (II)

in which R₇ is as defined above, with a derivative of formula (β):

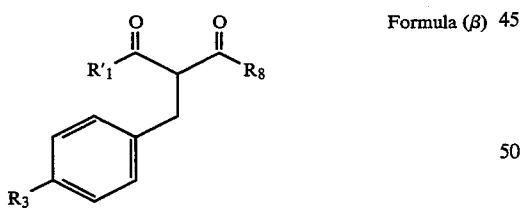

Formula (β)

in which R'₁ is a lower alkyl radical having 1 to 6 carbon atoms or an ether radical of the formula —(CH$_2$)$_p$—OR, in which p is an integer from 1 to 6 and R is a lower alkyl radical having 1 to 6 carbon atoms or a benzyl radical, R₈ is a lower alkyl radical having 1 to 6 carbon atoms or a lower O-alkyl group having 1 to 6 carbon atoms, preferably methyl or ethyl, and R₃ is as defined above, in an aprotic solvent such as dichloro- or trichloro-benzene, or in an acid solvent such as acetic acid, or else in an alcohol in the presence of the corresponding sodium or potassium alcoholate, or else in pyridine or 2-methyl-5-ethylpyridine in the presence or absence of 4-dimethylaminopyridine, at a temperature of between 50° and 200° C.;

b) if appropriate, protecting the group carried by R₃ using a method known per se;

c) heating the derivative thus obtained from the derivative of formula (β), when the latter is a ketoester, in an appropriate reagent such as, for example, POCl₃, to convert the hydroxyl group represented by A or B to a chlorine atom;

d) heating this chlorinated derivative in the presence of a nucleophile containing nitrogen, oxygen or sulfur, under reflux in an alcohol or in an autoclave at 100° C., in the presence or absence of a base such as, for example, Na₂CO₃, to give a derivative of formula (α) in which A and B have the same meanings as R₁ and R₂ respectively;

e) if appropriate, deprotecting the group carried by R₃;

e₁) converting this group to an acid group, for example by hydrolysis in the case where this group is a nitrile; or e₂) converting this group to a tetrazole group, for example, in the case where this group is a nitrile, by reaction with a trialkyltin azide with heating in toluene or xylene, followed by a treatment with gaseous hydrochloric acid in tetrahydrofuran; or e₃) converting this group to an amide group, for example, in the case where this group is a nitrile, by reaction with sulfuric acid, or by reaction with hydrogen peroxide, or else by reaction with polyphosphoric acid; and f) if appropriate, converting the resulting derivative to an addition salt, preferably a pharmaceutically acceptable addition salt.

According to the invention, it will be possible to synthesize the compounds of formula (I) in accordance with the following reaction sequence:

Methods known per se, such as, for example, the Claisen reaction or the method using Meldrum's acid, which methods can easily be found in the following literature references:

HAUSER C. R.; SWAMER F. W.; ADAMS J. T.; Org. Reaction, vol. VIII, 1954, 59–196, HENNE A. L.; TEDDER J. M.; J. Chem. Soc., 1953, 3628, BRESLOW D. S.; BAUMGARTEN E.; HAUSER C. R.; J. Am. Chem. Soc., 1944, 66, 1286, OIKAWA Y.; SUGANO K.; YONEMITSU O.; J. Org. Chem., 1978, 43(10), 2087–88, WIERENGA W.; SKULNICK H. I.; J. Org. Chem., 1979, 44, 310,

HOUGHTON R.; LAPHAM D.; SYNTHESIS, 1982, 6, 451–2,

BRAM G.; VILKAS M.; Bull. Soc. Chim. France, 1964(5), 945–51,

BALYAKINA M. V.; ZHDANOVICH E. S.; PREOBRAZHENSKII N. A.; Tr. Vses. Nauchn. Issled. Vitam in. Inst., 1961, 7, 8–16, RENARD M.; MAQUINAY A.; Bull. Soc. Chim. Belg., 1946, 55, 98–105, BRUCE F. W.; COOVER H. W.; J. Am. Chem. Soc., 1944, 66, 2092–94, and EBY C. J. and HAUSER C. R.; J. Am. Chem. Soc., 1957, 79, 723–5, will be used to prepare the compounds of formula (III):

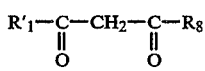 Formula (III)

in which R'₁ is a lower alkyl radical having 1 to 6 carbon atoms or an ether radical of the formula —(CH₂)ₚ—OR, in which p is an integer from 1 to 6 and R is a lower alkyl radical having 1 to 6 carbon atoms or a benzyl radical, and R₈ is a lower alkyl radical having 1 to 6 carbon atoms or a lower O-alkyl group having 1 to 6 carbon atoms, preferably methyl or ethyl.

The compounds of the formula

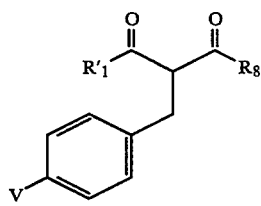 Formula (V)

will be obtained by benzylating the compounds of formula (III) with compounds of formula (IV):

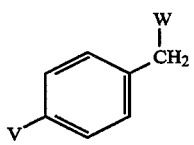 Formula (IV)

in the presence of a base such as sodium or potassium carbonate in acetone, a sodium or potassium alcoholate in an alcohol, or sodium or lithium hydride in solvents such as tetrahydrofuran, dioxane or dimethylformamide, for example, at a temperature of between 50° and 100° C., or else in the presence of one equivalent of lithium chloride or bromide and two equivalents of diisopropylethylamine in tetrahydrofuran under reflux, according to the following reference:

SUNG-EUN YOO; KYU YANG YI; Bull. Korean Chem. Soc., 1989, 10(1), 112.

These compounds of formula (V) can also be obtained by condensation of an aldehyde of formula (VI):

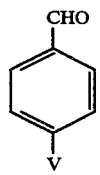 Formula (VI)

with the compounds of formula (III), followed by hydrogenation in the presence of a catalyst such as Raney nickel, palladium-on-charcoal or platinum oxide, in a solvent such as an alcohol or tetrahydrofuran, under pressure or at ordinary pressure if the substituents present allow it.

In more general terms, methods of preparing the compounds of formula (V) will be found in the following references:

DURGESHWARI P.; CHAUDHURY N. D.; J. Ind. Chem. Soc., 1962, 39, 735–6,

HEINZ P.; KREGLEWSKI A.; J. Prakt. Chem., 1963, 21(3–4), 186–197,

ZAUGG H. E.; DUNNIGAN D. A.; MICHAELS R. J.; SWETT L. R.; J. Org. Chem., 1961, 26, 644–51, KAGAN H. B.; HENG SUEN Y.; Bull. Soc. Chim. France, 1966(6), 1819–22, RATHKE M. W.; DEITCH J.; Tetrahedron Lett., 1971(31), 2953–6, BORRIES KUBEL; Liebigs Ann. Chem., 1980, 1392–1401, MARQUET J.; MORENO-MANAS M.; Chem. Lett., 1981, 2, 173–6, IOFFE T.; POPOV E. M.; VATSURO K. V.; TULIKOVA E. K.; KABACHNIK M. I.; Tetrahedron, 1962, 18, 923–940, and SHEPHERD T. M.; Chem. Ind. (London), 1970, 17, 567.

In formula (IV), W is a halogen atom, preferably chlorine or bromine.

In the same formula:

V can be a group

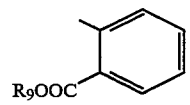

R₉ being a lower alkyl or benzyl radical, in which case the compounds of formula (IV) are prepared by reacting a magnesium compound of p-bromotoluene with a compound of the formula

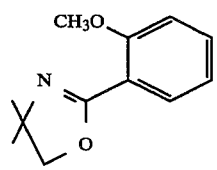

to give a compound of the formula

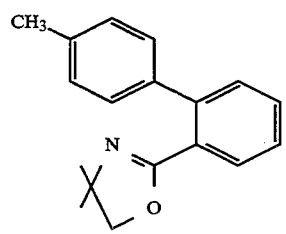

which is then hydrolyzed to give the compound of the formula

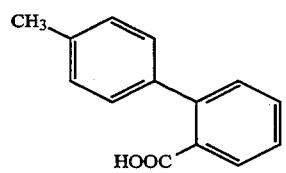

Procedures for the three steps described above will be found in the following reference:

MEYERS A. I.; MIHELICH E. D.; J. Am. Chem. Soc., 1975, 97, 7383.

The acid is then esterified with an alcohol of the formula R₉OH, R₉ being as defined above.

These derivatives are then brominated or chlorinated, for example with N-bromosuccinimide, N-chlorosuccinimide or bromine, in a solvent such as carbon tetrachloride, dibromoethane or dichloroethane, to give the compounds of formula (IV) in which V is the group

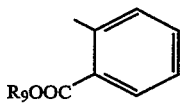

V can be the group

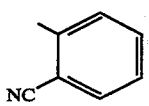

in which case the compound

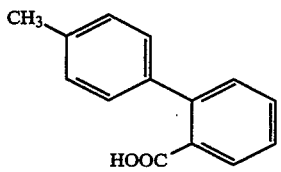

prepared above will be converted to the primary amide by reacting the acid chloride, obtained with thionyl chloride or phosphorus oxychloride, with aqueous ammonia, and this amide will be converted to the nitrile by reaction with phosphorus oxychloride in dimethylformamide or with thionyl chloride. Likewise, the compound

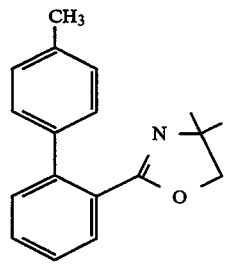

obtained above may be converted directly to the carbonitrile derivative by treatment in pyridine in the presence of POCl₃. The resulting nitrile derivative of the formula

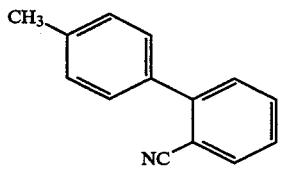

will then be brominated or chlorinated under the same conditions as the above ester to give the compounds of formula (IV) in which V is the group

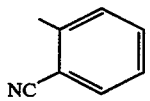

V can be a group

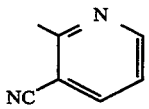

in which case the corresponding compounds of formula (IV) are synthesized in the following manner:

The magnesium compound

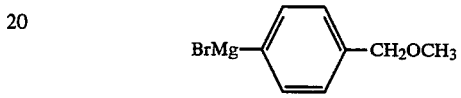

prepared by a conventional Grignard reaction, is converted to the zinc derivative by reaction with zinc chloride. This zinc derivative is condensed with 2-chloronicotinonitrile, in the presence of [Ni(PΦ₃)]₂Cl₂, to give the derivative of the formula

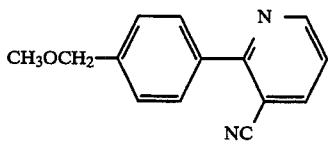

This compound, treated with boron tribromide in chloroform, will give the compounds of formula (IV) in which W is the bromine atom and V is the group

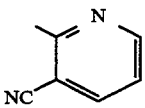

V can be a group

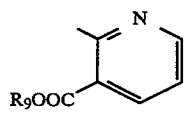

R₉ being as defined above, in which case the corresponding compounds of formula (IV) may be prepared from the nitrile prepared above of the formula

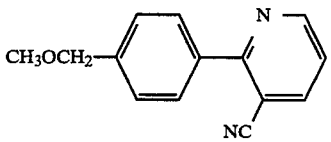

by conventional hydrolysis of the nitrile group followed by esterification of the acid obtained, or direct conversion of the nitrile group to the ester group by the methods known to those skilled in the art, followed by a treatment with boron tribromide in chloroform, to give the compounds of formula (IV) in which W is the bromine atom and V is the group

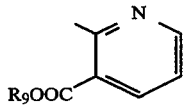

V can be a group

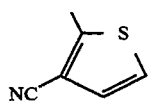

in which case the corresponding compounds of formula (IV) are synthesized in the following manner:

The compound of the formula

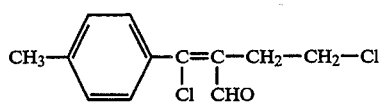

will be obtained from 4-chloro-4'-methylbutyrophenone of the formula

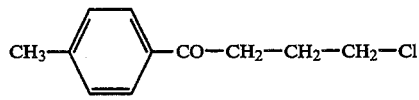

the preparation of which is described in Belgian patent 577,977 of May 15, 1959, CA: 54, 4629 c, by treatment with phosphorus oxychloride and dimethylformamide under the conditions described in the following reference:

VOLODINA M. A.; TENENT'EV A. P.; KUDRYASHOVA V. A.; KABOSHINA L. N.; Khim. Geterosikl. Soedim; 1967, 5-8.

This compound is then treated with sodium sulfide in a solvent such as tetrahydrofuran, under reflux, to give the derivative

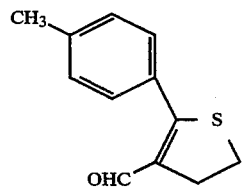

which is then converted in two steps to the nitrile derivative by dehydration of the oxime formed from the aldehyde and hydroxylamine. This dehydration may be carried out for example with acetic anhydride to give the nitrile compound

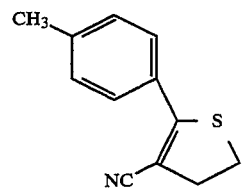

which may then be aromatized by treatment with bromine in carbon tetrachloride to give the compound

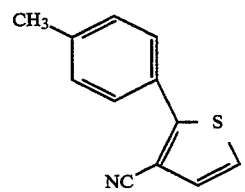

This compound can then be chlorinated or brominated with halogenating agents such as N-chlorosuccinimide or N-bromosuccinimide, in a solvent such as carbon tetrachloride or dibromoethane, to give the compounds of formula (IV) in which V is the group

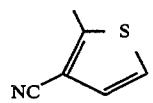

V can be a group

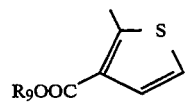

$R_9$ being as defined above, in which case the corresponding compounds of formula (IV) may be prepared from the nitrile prepared above of the formula

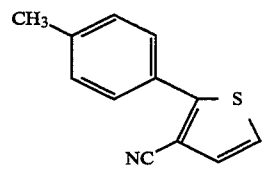

by conventional hydrolysis of the nitrile group followed by esterification of the acid obtained, or direct conversion of the nitrile group to the ester group by the methods known to those skilled in the art, followed by chlorination or bromination of the ester with N-chlorosuccinimide or N-bromosuccinimide, for example in carbon tetrachloride or dibromoethane, to give the compounds of formula (IV) in which W is the bromine atom or the chlorine atom and V is the group

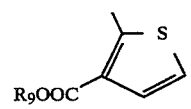

V can be a group

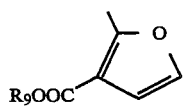

$R_9$ being as defined above, in which case the corresponding compounds of formula (IV) may be prepared by reacting the diazotized derivative of p-toluidine with 3-furoic acid to give the compounds of the formula

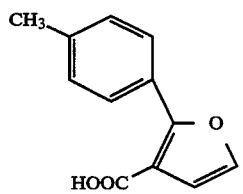

by the method described in the following literature reference:

A. JURASEK et al., Collect. Czech. Chem. Commun., 1989, 54, 215.

This compound will then be esterified by the conventional methods known to those skilled in the art to give the compound

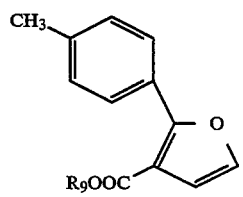

in which $R_9$ is as defined above, this derivative then being brominated or chlorinated by reaction with N-bromosuccinimide or N-chlorosuccinimide, for example in carbon tetrachloride or 1,2-dichloroethane, to give the derivative of formula (IV) in which W is the bromine atom or the chlorine atom and V is the group

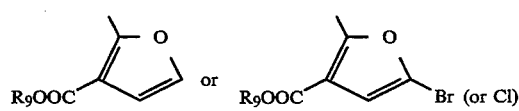

V can be a group

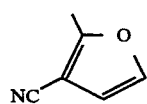

in which case the acid

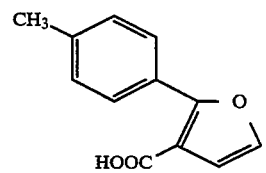

prepared above will be converted to the acid chloride by reaction with thionyl chloride and then to the amide by reaction with ammonia. The amide obtained will be converted to the nitrile by reaction with phosphorus oxychloride in dimethylformamide to give the compounds of the formula

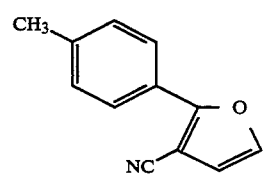

This derivative will then be brominated or chlorinated by reaction with N-bromosuccinimide or N-chlorosuccinimide, for example in carbon tetrachloride or 1,2-dichloroethane, to give the compounds of formula (IV) in which W is the bromine atom or the chlorine atom and V is the group

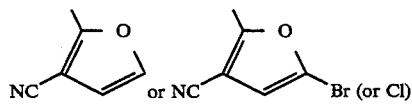

In formula (V), $R'_1$ and $R_8$ are as defined above and V is as defined in formula (IV).

However, the compounds of formula (V) in which V is a group

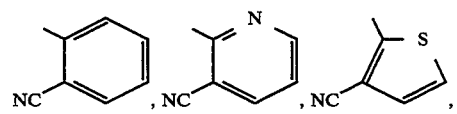

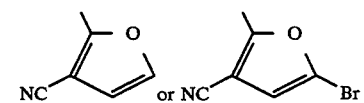

will react with one equivalent of sodium azide in a solvent such as dimethylformamide, in the presence of an ammonium salt such as ammonium chloride, or by heating in toluene or xylene with a trialkyltin azide, to give the compounds of formula (V) in which V is the group

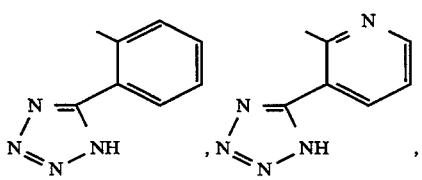

In formula (VI), V is as defined in formula (IV), but this condensation method will only be used when V possesses a group unaffected by hydrogenation.

Thus reaction of a 3-amino-1,2,4-triazole of formula (II):

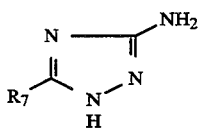  Formula (II)

in which R$_7$ is as defined above (these products being commercially available or capable of being prepared by the methods described in the following literature references:

HUFFMANN and SCHAEFER, J. of Org. Chem., 1963, 28, p. 1812–1816 and p. 1816–1821, ALLEN et al., J. of Org. Chem., 1959, 24, p. 793–796, and Organic Synthesis Collective, volume 3, p. 95), with the compounds of formula (V), in which R'$_1$ and R$_8$ are as defined above and V is one of the following groups:

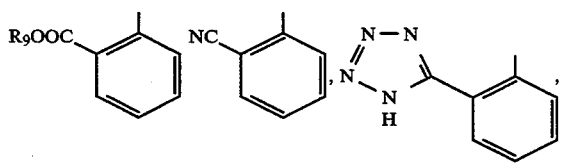

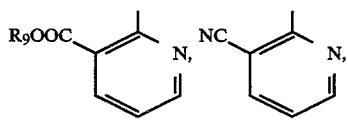

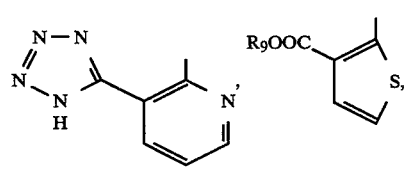

where R$_9$ is as defined above, will give the compounds of formulae (VIIa) and/or (VIIb):

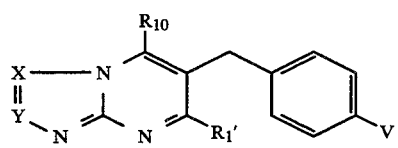  Formula (VIIa)

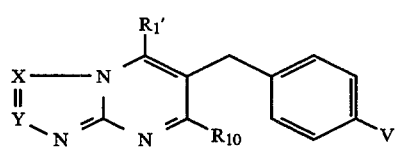  Formula (VIIb)

and their tautomeric forms, in which R'$_1$, X, Y and V are as defined above and R$_{10}$ is the hydroxyl group when the compounds of formula (V) are β-ketoesters and a lower alkyl radical having 1 to 6 carbon atoms in the case where these same compounds of formula (V) are β-diketones, by condensation in an aprotic solvent such as dichloro- or trichloro-benzene, or in an acid solvent such as acetic acid, or else in an alcohol in the presence of the corresponding sodium or potassium alcoholate, or else in pyridine or 2-methyl-5-ethyl-pyridine in the presence or absence of 4-dimethylaminopyridine, at a temperature of between 50° and 200° C.

In the case where V possesses a tetrazole group, the reaction temperatures should not exceed 140° C. so as not to decompose the tetrazole.

The reactions of aminotriazoles or similar heteroaromatic amines with β-ketoesters and β-diketone derivatives are described well in the literature and, according to the operating conditions, the forms obtained are identified. Examples which may be cited are the studies by J. A. VAN ALLAN et al., J. Org. Chem., p. 779 to p. 801 (1959), and by L. A. WILLIAMS, J. Chem. Soc., p. 1829 (1960), and L. A. WILLIAMS, J. Chem. Soc., p. 3046 (1961).

Thus the compounds VIIa and VIIb will be identified for separate treatment.

The Applicant has discovered, however, that 2-methyl-5-ethylpyridine, in the presence or absence of 4-dimethylaminopyridine, is a preferred solvent for orientating the reaction almost exclusively towards the formation of the derivatives of formula (VIIb); in fact, the temperature (170°–180° C.) and the pH which are necessary for this orientation can be achieved using this solvent.

If the derivatives of formulae (VIIa) and (VIIb) in which R$_{10}$ is a hydroxyl group are treated with a reagent such as P$_2$S$_5$ or Lawesson's reagent, the derivatives of formulae (VIIa) and (VIIb) in which the group R$_{10}$ is a thiol will be obtained.

For example, if the derivatives of formulae (VIIa) and (VIIb) in which R$_{10}$ is a hydroxyl group are heated in POCl$_3$, the derivatives of formulae (VIIIa) and (VIIIb):

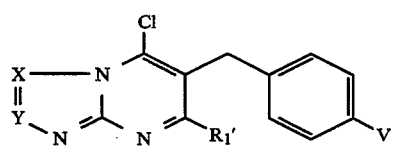

Formula (VIIIa)

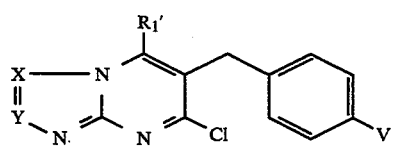

Formula (VIIIb)

will be obtained, in which R'$_1$, X, Y and V are as defined above.

Hydrogenation of the derivatives of formulae (VIIIa) and (VIIIb), in the presence of a catalyst such as Palladium-on-charcoal, will make it possible to replace the chlorine with a hydrogen atom, and the derivatives of formula (IX):

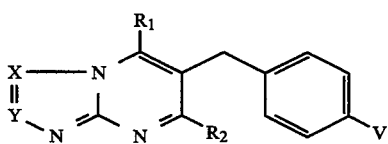

Formula (IX)

in which R$_1$, R$_2$, X, Y and V are as defined above, will be obtained by heating the derivatives of formulae (VIIIa) and (VIIIb), in the presence of a nucleophile containing nitrogen, oxygen or sulfur, under reflux in an alcohol, in the presence or absence of a base such as Na$_2$CO$_3$, or in an autoclave at 100° C.

The derivatives of formulae (VIIa) and (VIIb) in which R'$_1$ is the group (CH$_2$)$_p$O-benzyl, p being as defined above, may be hydrogenated in the presence of palladium-on-charcoal, in acetic acid, to give the compounds of formulae (VIIa) and (VIIb) in which R'$_1$ is an alcohol group.

These triazolopyrimidines of formulae (VIIa) and (VIIb) may also be obtained by reacting the derivatives of formula (X):

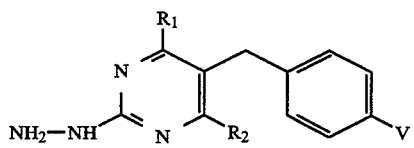

Formula (X)

in which R$_1$, R$_2$ and V are as defined above, with:
acids, acid chlorides or carboxylic acid esters,
isocyanates or isothiocyanates,
orthoesters,
carbonyldiimidazole or
urea, potassium xanthogenate, carbon disulfide or an analogous reagent, by heating without a solvent or in a solvent such as N-methylpyrrolidone or an alcohol like ethanol or methoxyethanol, in the presence or absence of a base such as triethylamine, pyridine or 2-methyl-5-ethylpyridine.

Depending on the operating conditions, especially the temperature and pH of the reaction, 1,2,4-triazolo[4,3-a]pyrimidine derivatives or their 1,2,4-triazolo[1,5-a]pyrimidine rearrangement products will be obtained.

The compounds of formula (X) can be obtained by any one of the known methods of synthesizing 2-hydrazinopyrimidines (cf.: The Pyrimidines; The Chemistry of Heterocyclic Compounds; D. J. BROWN; Wiley Interscience 1970), especially by substituting the derivatives of formula (XI):

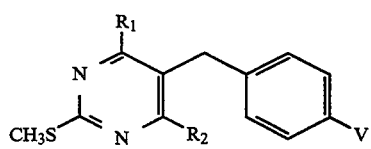

Formula (XI)

in which R$_1$, R$_2$ and V are as defined above, with hydrazine hydrate, for example.

The compounds of formula (XI) are obtained by condensing S-methylthiourea with the derivatives of formula (V), for example, or by any one of the methods of synthesizing 2-thiomethylpyrimidines which are known in the literature (cf.: The Pyrimidines, op. cit.).

The compounds of formula (IX) in which V possesses an ester group COOR$_9$ may be hydrolyzed in an acid or basic medium, or hydrogenated in the case where R$_9$ is a benzyl, to give the compounds of formula (I) in which R$_3$ possesses an acid group.

The compounds of formula (IX) in which V possesses a nitrile group will react with one equivalent of sodium azide in a solvent such as dimethylformamide, in the presence of an ammonium salt such as ammonium chloride, or by heating in toluene or xylene with a trialkyltin azide, for example trimethyltin or tributyltin azide, followed by an acid treatment, for example with gaseous hydrochloric acid in tetrahydrofuran, to give the compounds of general formula (I) in which R$_3$ possesses a tetrazol-5-yl group.

These same compounds in which V possesses a nitrile group may be converted by reaction with sulfuric acid, or by reaction with hydrogen peroxide, or else by reaction with polyphosphoric acid, to derivatives of general formula (I) in which R$_3$ possesses an amide group.

The derivatives in which V possesses a nitrile group or an amide group may also be converted by basic or acid hydrolysis to derivatives of general formula (I) in which $R_3$ possesses an acid group.

It is possible to obtain addition salts of some of the compounds of formula (I), especially pharmaceutically acceptable addition salts. In particular, when the compounds of formula (I) contain an acid or tetrazole group, there may be mentioned the salts of sodium, potassium, calcium, an amine such as dicyclohexylamine or an amino acid such as lysine. When they contain an amine group, there may be mentioned the salts of an inorganic or organic acid, such as, for example, the hydrochloride, methanesulfonate, acetate, maleate, succinate, fumarate, sulfate, lactate or citrate.

The novel compounds according to the invention possess remarkable pharmacological properties as angiotensin II receptor antagonists and antiproliferatives and can be used in therapeutics for the treatment and prevention of cardiovascular diseases and in particular for the treatment of hypertension, cardiac insufficiency and diseases of the arterial wall, especially atherosclerosis.

Thus the invention covers the pharmaceutical compositions which contain as the active principle the drugs consisting of a pharmaceutically effective amount of at least one compound of formula (I) as defined above, as well as one of its pharmaceutically acceptable addition salts where appropriate.

These compositions can be administered by the buccal, rectal, parenteral, transdermal or ocular route.

These compositions can be solid or liquid and can take the pharmaceutical forms commonly used in human medicine, such as, for example, simple or coated tablets, gelatin capsules, granules, suppositories, injectable preparations, transdermal systems and eye lotions. They are prepared by the customary methods. In said compositions, the active principle, consisting of a pharmaceutically effective amount of at least one compound of formula (I) as defined above, or one of its pharmaceutically acceptable addition salts, can be incorporated with excipients normally employed in these pharmaceutical compositions, such as talc, gum arabic, lactose, starch, magnesium stearate, polyvidone, cellulose derivatives, cacao butter, semisynthetic glycerides, aqueous or non-aqueous vehicles, fats of animal or vegetable origin, glycols, various wetting agents, dispersants or emulsifiers, silicone gels, certain polymers or copolymers, preservatives, flavorings and colors.

The invention also covers a pharmaceutical composition with antagonistic activity towards angiotensin II receptors, and/or antiproliferative activity, which permits especially a favorable treatment or prevention of cardiovascular diseases, in particular hypertension, cardiac insufficiency and diseases of the arterial wall, especially atherosclerosis, said composition comprising a pharmaceutically effective amount of at least one compound of formula (I) given above, or one of its pharmaceutically acceptable addition salts, which may be incorporated in a pharmaceutically acceptable excipient, vehicle or carrier.

The dosage varies especially according to the route of administration, the complaint treated and the subject in question.

For example, for an adult with an average weight of 60 to 70 kg, it can vary between 1 and 400 mg of active principle, administered orally in one or more daily doses, or from 0.01 to 50 mg, administered parenterally in one or more daily doses.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. This pharmaceutical composition can be formulated as gelatin capsules or tablets containing from 1 to 400 mg of active principle, or as injectable preparations containing from 0.01 to 50 mg of active principle.

The invention also covers a method of therapeutic treatment for mammals, which comprises administering to this mammal a therapeutically effective amount of at least one compound of formula (I) as defined above, or one of its pharmaceutically acceptable addition salts.

In animal therapeutics, the daily dose which can be used is normally between 1 and 100 mg per kg.

Further characteristics and advantages of the invention will be understood more clearly from the following description of some Preparatory Examples, which in no way imply a limitation but are given by way of illustration.

EXAMPLE 1

Ethyl 3-oxohexanoate

Formula (III):
$R'_1$=n-propyl, $R_8$=O-ethyl 176 g of 2,2-dimethyl-4,6-dioxo-1,3-dioxane (Meldrum's acid) are dissolved in 550 ml of dichloromethane and 188 ml of pyridine; the mixture is cooled to 5° C. with a bath of water and ice and 133 ml of butyryl chloride are added dropwise. When the addition is complete, the mixture is stirred for three hours at room temperature. The solution is washed with a dilute solution of hydrochloric acid, dried over magnesium sulfate and evaporated under vacuum to give an oil. This oil is dissolved in 700 ml of ethanol and the mixture is refluxed for six hours. The ethanol is evaporated off under vacuum and the residue obtained is distilled to give 145.4 g of ethyl 3-oxohexanoate in the form of an oil.

Boiling point (20 mm of mercury): 98°–100° C.

The compound of Example 2 was prepared by the procedure of Example 1.

EXAMPLE 2

Ethyl 3-oxoheptanoate

Formula (III):
$R'_1$=n-butyl, $R_8$=O-ethyl
Boiling point (20 mm of mercury): 115°–120° C.

EXAMPLE 3

Ethyl 4-benzyloxy-3-oxobutanoate

Formula (III): $R_1'$ = CH$_2$—O—CH$_2$—

$R_8$ = O-ethyl 80 g of 60% NaH are added in portions to 800 ml of anhydrous THF. The medium is cooled to 10° C. and maintained at this temperature. 500 ml of benzyl alcohol are then introduced dropwise. A solution of 65.8 g of ethyl 4-chloroacetoacetate in 200 ml of benzyl alcohol is then added. The mixture is stirred at room temperature for 20 h. It is neutralized by the slow addition of acetic acid (120 ml) while being cooled with an ice bath. The whole is then poured into a mixture of water and ice and extracted with ether. The organic phase is washed with a solution of sodium bicarbonate, dried over MgSO4 and then concentrated to give an orange oil. The product is purified by two successive distillations to give a yellow oil.

Boiling point (under 0.05 mm of mercury): 126°–132° C.

EXAMPLE 4

4'-Bromomethyl-2-cyanobiphenyl

Formula (IV):
W=Br,

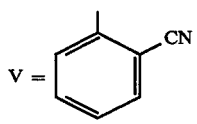

a) Preparation of 2-cyano-4'-methylbiphenyl 563.8 g of (4'-methylbiphenyl-2-yl)carboxylic acid, prepared according to MEYERS A. I.; MIHELICH E. D.; J. Am. Chem. Soc., 1975, 97(25), 7383, are added in small portions to 800 ml of thionyl chloride. The mixture is refluxed for two hours. The thionyl chloride is concentrated under vacuum and the residue is poured into a 28% solution of ammonium hydroxide cooled beforehand with a bath of water and ice. The mixture is stirred for 30 minutes and the crystals obtained are filtered off, washed with water followed by ether and then dried to give 554.8 g of (4'-methylbiphenyl-2-yl)-carboxamide in the form of crystals melting at 128°–132° C. These crystals are taken up in 1300 ml of thionyl chloride and the mixture is refluxed for 3 hours and then concentrated under vacuum to give an orange oil. This is taken up in two liters of chloro-form and washed with water and the organic phase is then dried and concentrated to give 509.8 g of an oil, which crystallizes from pentane to give 467.3 g of 2-cyano-4'-methylbiphenyl.

Melting point: 46°–48° C.

b) 4'-Bromomethyl-2-cyanobiphenyl 467.3 g of 2-cyano-4'-methylbiphenyl, prepared above, are dissolved in 4.7 l of 1,2-dichloroethane in the presence of 467.3 g of N-bromosuccinimide and 9.3 g of benzoyl peroxide. The mixture is heated very gradually so as to have good control over the exothermic effect. It is subsequently refluxed for 4 h, cooled to 50° C. and then washed 3 times with hot water and dried and the organic phase is concentrated to give cream-colored crystals.

Recrystallization from isopropanol gives 451 g of white crystals of 4'-bromomethyl-2-cyanobiphenyl.

Melting point: 128° C.

EXAMPLE 5

Ethyl 2-[(2'-cyanobiphenyl-4-yl)methyl]-3-oxohexanoate

Formula (V):
R'1=n-propyl, R8=O-ethyl,

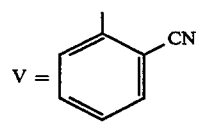

23 g of ethyl 3-oxohexanoate, prepared in Example 1, are dissolved in 120 ml of tetrahydrofuran. 30.3 g of 4'-bromomethyl-2-cyanobiphenyl, prepared in Example 4, and 4.7 g of lithium chloride are added and the mixture is stirred at room temperature. 39 ml of diisopropylethylamine are then introduced dropwise, causing a slight exothermic effect. The mixture is subsequently stirred for three hours at room temperature and then for ten hours under reflux. The solvents are evaporated off under vacuum and the residue is taken up in water and then extracted with chloroform. The organic phase is decanted and then washed with a dilute solution of hydrochloric acid, dried over magnesium sulfate and evaporated under vacuum to give 38 g of an orange oil.

Purification by chromatography on silica gel (eluent: CHCl3) gives 32.3 g of ethyl 2-[(2'-cyanobiphenyl-4-yl)methyl]-3-oxohexanoate.

The compounds of Examples 6 to 10 are obtained by the procedure of Example 5 using the appropriate β-ketoester.

EXAMPLE 6

Ethyl 2-[(2'-cyanobiphenyl-4-yl)methyl]-3-oxoheptanoate

Formula (V):
R'1=n-butyl, R8=O-ethyl,

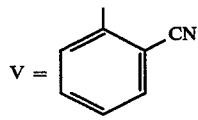

Oil used as such in the next step.

EXAMPLE 7

Ethyl 2-[(2'-cyanobiphenyl-4-yl)methyl]-3-oxobutanoate

Formula (V):
R'1=methyl, R8=O-ethyl,

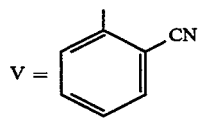

Yellow oil purified by chromatography on silica gel (eluent: chloroform 95%/ether 5%).

EXAMPLE 8

Ethyl 2-[(2'-cyanobiphenyl-4-yl)methyl]-3-oxopentanoate

Formula (V):
R'1=ethyl, R8=O-ethyl,

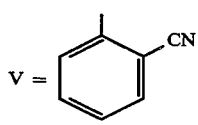

Oil purified by chromatography on silica gel (eluent: CHCl₃ 95%/ether 5%).

EXAMPLE 9

Ethyl 2-[(2′-cyanobiphenyl-4-yl)methyl]-4-methoxy-3-oxobutanoate

Formula (V):
R′$_1$ = methoxymethyl, R$_8$ = O-ethyl,

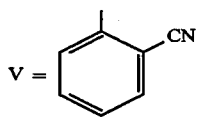

Yellow oil purified by chromatography on silica gel (eluent: CHCl₃ 95%/ether 5%).

EXAMPLE 10

Ethyl 4-benzyloxy-2-[(2′-cyanobiphenyl-4-yl)methyl]-3-oxobutanoate

Formula (V): R′$_1$ = CH$_2$—O—CH$_2$—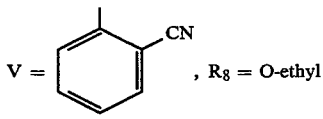

, R$_8$ = O-ethyl

Oil purified by chromatography twice in succession (eluents: chloroform, then cyclohexane 80%/ethyl acetate 20%).

EXAMPLE 11

Ethyl 2-[4-(3-cyano-2-pyridyl)benzyl]-3-oxohexanoate

Formula (V): R′$_1$ = CH$_2$—CH$_2$—CH$_3$, V = 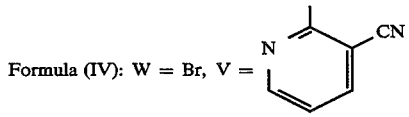,

R$_8$ = O-ethyl a) Preparation of 4-bromobenzyl methyl ether

A solution of sodium methylate, prepared from 11.8 g of sodium and 350 ml of methanol, is introduced dropwise into a suspension of 117.7 g of 4-bromobenzyl bromide in 350 ml of methanol. The mixture is stirred for 2 h at room temperature and left to stand overnight. The methanol is evaporated off, the residue is taken up in ether and the organic phase is washed with water and then dried and concentrated to give a yellow oil, which is purified by distillation to give 102 g of bromobenzyl methyl ether as a colorless liquid.

Boiling point under 17 mm of mercury: 112°–114° C.

b) Synthesis of 3-cyano-2-(4-methoxymethylphenyl)pyridine 2 g of the compound 4-bromobenzyl methyl ether, prepared above, are added to a suspension of 18 g of magnesium in 50 ml of anhydrous THF. The formation of the magnesium compound is initiated with a few crystals of iodine and, if necessary, by heating with a bath of warm water. A solution of 121.8 g of 4-bromobenzyl methyl ether in 200 ml of anhydrous THF is introduced dropwise so that the temperature does not exceed 40° C. The components are reacted for 1 h at room temperature and 800 ml of a solution of zinc chloride in ether are then introduced under excess nitrogen pressure. A white precipitate forms. The components are reacted for 1 h 30 min at room temperature. 800 mg of the coupling catalyst bis(triphenylphosphine)nickel-(II) chloride, [NiP(phenyl)$_3$]$_2$Cl$_2$, are added and a solution of 76.9 g of 2-chloronicotinonitrile in 300 ml of THF is then introduced. The mixture is stirred overnight at room temperature and concentrated under vacuum. The concentrate is taken up in a mixture of 1 l of dichloromethane, 1 l of water and 1 l of the disodium salt of EDTA. The emulsion is filtered on Célite 545. The organic phase is decanted, washed with water, dried and concentrated to give 133.6 g of an orange oil, which is purified by chromatography twice in succession (eluent: chloroform 95%/ether 5%). 69.4 g of 3-cyano-2-(4-methoxymethylphenyl)pyridine are thus isolated in the form of an orange oil, which crystallizes.

Melting point: 74° C.

c) Preparation of 3-cyano-2-(4-bromomethylphenyl)pyridine

Formula (IV): W = Br, V = 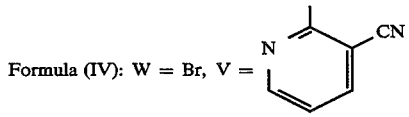

69.4 g of 3-cyano-2-(4-methoxymethylphenyl)pyridine, prepared in the previous step, are dissolved in 700 ml of chloroform stabilized with amylene. The solution is cooled to −10° C. A solution of 66 ml of BBr$_3$ in 200 ml of chloroform stabilized with amylene is introduced dropwise so that the temperature does not exceed 5° C. The mixture is left for 1 h 30 min in an ice bath. It is hydrolyzed with ice and then with water. It is filtered and the suspension is taken up in a mixture of water and chloroform. After decantation, the organic phases are combined, dried and then concentrated to give 78.2 g of cream-colored crystals of 3-cyano-2-(4-bromomethylphenyl)pyridine.

Melting point: 118° C.

d) Preparation of ethyl 2-[4-(3-cyano-2-pyridyl)benzyl]-3-oxohexanoate

Formula (V): R′$_1$ = CH$_2$—CH$_2$—CH$_3$, V = 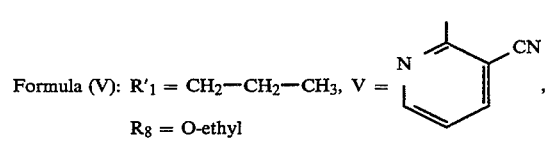,

R$_8$ = O-ethyl

Following the procedure of Example 5, the expected derivative is obtained in the form of an orange oil, which is used as such in the next step.

EXAMPLE 12

Ethyl 2-[4-(3-cyano-2-thienyl)benzyl]-3-oxohexanoate

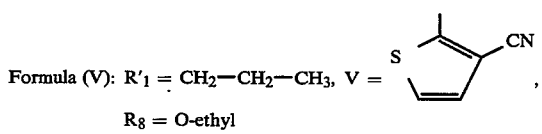

Formula (V): R'₁ = CH₂—CH₂—CH₃, V =

R₈ = O-ethyl a) Preparation of 4-chloro-1-(4-methylphenyl)butanone

A mixture of 560 ml of 4-chlorobutyryl chloride and 550 ml of toluene is added dropwise to a suspension of 740 g of AlCl₃ in 2 l of dichloromethane, the temperature being maintained at between 10° and 15° C. The reaction mixture is stirred for 30 min at room temperature and poured on to ice. After decantation, the organic phase is separated off and the aqueous phase is extracted with dichloromethane. The organic phases are combined, washed with water and then dried and concentrated under vacuum to give 994.5 g of 4-chloro-1-(4methylphenyl)butanone in the form of an oil, which is used in the next step without further purification.

b) Preparation of 3-chloro-2-(2-chloroethyl)-3-(4-methylphenyl)prop-2-en-1-al 390 ml of POCl₃ are introduced dropwise, at a temperature of between 7° and 12° C., into a solution of 352.5 g of 4-chloro-1-(4-methylphenyl)butanone, prepared above according to Example 12a), in 450 ml of DMF. The temperature is raised gradually, in the first instance to 50° C. over 2 h and then to 75° C. over 45 min. The mixture is poured on to ice and extracted three times with ether and the organic phases are combined, washed with water and then dried and evaporated to give 387.8 g of 3-chloro-2-(2-chloroethyl)-3-(4-methylphenyl)prop-2-en-1-al in the form of an oil, which is used as such in the next step.

c) Preparation of 4,5-dihydro-3-formyl-2-(4-methylphenyl)thiophene

A mixture of 200 g of 3-chloro-2-(2-chloroethyl)-3-(4-methylphenyl)prop-2-en-1-al, prepared in Example 12b), 2.2 l of THF, 276.5 g of Na₂S.9H₂O and 373 ml of water is refluxed for 6 h. It is concentrated under vacuum and the concentrate is taken up in water and extracted 3 times with ether. The organic phases are combined, washed with water, dried and concentrated to give 170.3 g of an oil, which crystallizes.

Melting point: below 50° C.

d) Preparation of 4,5-dihydro-3-formyl-2-(4-methylphenyl)thiophene oxime 132.1 g of hydroxylamine hydrochloride are added in portions to a solution of 323.5 g of the aldehyde prepared according to 12c) in 800 ml of ethanol. A solution of sodium carbonate, prepared from 100.5 g of Na₂CO₃ and 700 ml of water, is then added dropwise. The mixture is heated at 40° C. for 5 min and the reaction is then left to proceed at room temperature for 1 h. The mixture is cooled to 15° C. and the solid is filtered off and washed with water and then with a mixture of isopropyl ether 50%/petroleum ether 50% to give 252 g of oxime. Extraction of the filtrate with dichloromethane gives a 2nd crop of 99 g of the expected oxime.

e) Preparation of 3-cyano-4,5-dihydro-2-(4-methylphenyl)thiophene

A solution of 171.8 g of the oxime prepared in Example 12d) in 680 ml of acetic anhydride is refluxed for 3 h. It is concentrated to remove the excess anhydride and then distilled to give 115.3 g of nitrile derivative.

Boiling point under 0.05 mm of mercury: 140°-150° C.

f) Preparation of 3-cyano-2-(4-methylphenyl)thiophene 62 ml of bromine are introduced dropwise into a solution, preheated to 50° C., of 191.3 g of the nitrile prepared according to Example 12e) in 1.85 l of CCl₄. The whole is refluxed until the evolution of HBr ceases. The CCl₄ is evaporated off and the residue is distilled to give 115.3 g of 3-cyano-2-(4-methylphenyl)thiophene.

Boiling point under 0.05-0.1 mm of mercury: 130°-150° C.

g) 2-(4-Bromomethylphenyl)-3-cyanothiophene

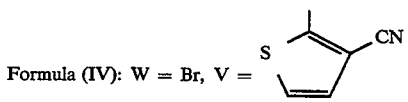

Formula (IV): W = Br, V =

182.2 g of the compound obtained in Example 12f) are brominated according to Example 4 to give 133.7 g of 2-(4-bromomethylphenyl)-3-cyanothiophene.

Melting point: 80°-84° C.

h) Ethyl 2-[4-(3-cyano-2-thienyl)benzyl]-3-oxohexanoate

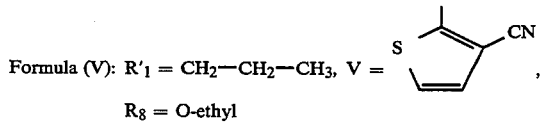

Formula (V): R'₁ = CH₂—CH₂—CH₃, V =

R₈ = O-ethyl

A mixture of 50 g of 2-(4-bromomethylphenyl)-3-cyanothiophene, prepared above, 40 g of ethyl 3-oxohexanoate, prepared in Example 1, 300 ml of THF, 62 ml of diisopropylethylamine and 15.6 g of LiBr is refluxed for 15 h. It is concentrated under vacuum, a dilute solution of hydrochloric acid is added and the mixture is extracted with ethyl acetate. The organic phases are combined, washed with water, dried and evaporated to give 62.4 g of ethyl 2-[4-(3-cyano-2-thienyl)benzyl]-3-oxohexanoate in the form of an oil, which is used without further purification.

EXAMPLE 13

Ethyl 2-[4-(3-cyano-2-furyl)benzyl]-3-oxohexanoate

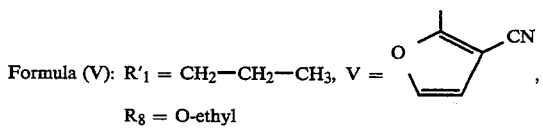

Formula (V): R'₁ = CH₂—CH₂—CH₃, V =

R₈ = O-ethyl a) Preparation of 2-(4-methylphenyl)-3-furanoic acid 70.7 g of p-toluidine, cooled with a bath of water and ice, are treated with 205 ml of 36% HCl. The mixture is then stirred at 55°-60° C. for 30 min before being cooled to 0° C. again. A solution of 45 g of NaNO₂ in 220 ml of water is then introduced. The mixture is stirred for 1 h at 0° C. This cold solution is introduced into a mixture of 49.3 g of 3-furanoic acid, 220 ml of acetone, 23.4 g of CuCl₂ and 6.3 g of water, cooled to −5° C. The whole is stirred at 0° C. for 2 h and then at room temperature for 48 h. It is extracted twice with ether and the organic phase is decanted, dried and concentrated to give an oil, which gives crystals when treated with water. The crystals are filtered off and washed with 50 ml of a 50% methanol/water mixture to give 13.4 g of 2-(4-methylphenyl)-3-furanoic acid.

Melting point: 166° C.

b) Preparation of 2-(4-methylphenyl)furan-3-carboxamide 20 ml of SOCl$_2$ are added to a solution of 13.4 g of the furanoic acid prepared above in 70 ml of toluene. The mixture is refluxed for 3 h and the excess SOCl$_2$ and the toluene are then distilled to give an oil, which is reacted at 5° C. with a solution of 100 ml of 1,2-dimethoxyethane saturated with ammonia. The precipitate is filtered off and washed with water and then with isopropyl alcohol to give 7 g of white crystals of amide.

Melting point: 174° C.

c) Preparation of 3-cyano-2-(4-methylphenyl)furan

A mixture of 12.2 g of the amide prepared above and 65 ml of SOCl$_2$ is refluxed for 3 h and concentrated under vacuum. The oil obtained is taken up in chloroform, and water and ice are then added. After decantation, the aqueous phase is extracted with chloroform and the organic phases are combined, dried and evaporated to give an oil. Purification by chromatography on silica gel (eluent: toluene) gives 7.5 g of an oil, which crystallizes.

Melting point: 66° C.

d) 2-(4-Bromomethylphenyl)-3-cyanofuran

Formula (IV): W = Br, V = 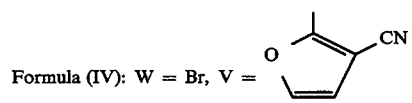

7.5 g of the compound obtained in Example 13 c) are brominated according to Example 4 to give, after purification by chromatography on silica gel (eluent: pentane 50%/toluene 50%), 4.6 g of 5-bromo-3-cyano-2-(4-methylphenyl)furan (melting point: 88° C.), 2.2 g of 5-bromo-3-cyano-2-(4-bromomethylphenyl)furan (melting point: 114° C.) and 2 g of 2-(4-bromomethylphenyl)-3-cyanofuran.

Melting point: 108° C.

The compound 5-bromo-3-cyano-2-(4-methylphenyl)furan is subjected to a further bromination reaction according to Example 4 to give 5-bromo-2-(4-bromomethylphenyl)-3-cyanofuran, which constitutes the compound of Example 13 d) bis.

e) Ethyl 2-[4-(3-cyano-2-furyl)benzyl]-3-oxohexanoate

Formula (V): R'$_1$ = CH$_2$—CH$_2$—CH$_3$, V = 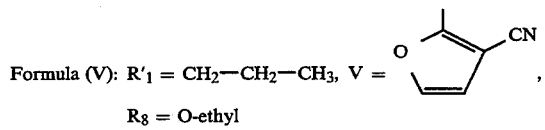, R$_8$ = O-ethyl

The resulting derivative 2-(4-bromomethylphenyl)-3-cyanofuran is treated according to Example 5 to give ethyl 2-[4-(3-cyano-2-furyl)benzyl]-3-oxo-hexanoate in the form of an oil, which is used in the crude state in the next step.

Likewise, the derivative 5-bromo-2-(4-bromomethylphenyl)-3-cyanofuran of Example 13 d) bis is treated according to Example 5 to give ethyl 2-[4-(5-bromo-3-cyano-2-furyl)benzyl]-3-oxohexanoate in the form of an oil, which constitutes the derivative of Example 13 bis.

EXAMPLE 14

3-[(2'-Cyanobiphenyl-4-yl)methyl]-2,4-dioxopentane

Formula (V): R'$_1$ = CH$_3$, R$_8$ = CH$_3$, V = 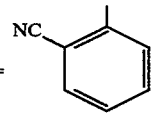

32.8 g of 2,4-dioxopentane, 68 g of 4'-bromomethyl-2-cyanobiphenyl, prepared in Example 4, 88 ml of diisopropylamine and 10.6 g of anhydrous lithium chloride in 300 ml of tetrahydrofuran are refluxed for 27 h. The mixture is cooled and the precipitate is filtered off. The organic phase is concentrated to dryness to give 88.5 g of crystals. These are taken up in isopropanol and the mixture is filtered to isolate 38.8 g of unreacted 4'-bromomethyl-2-cyanobiphenyl. The concentrated mother liquors yield 26.5 g of an oil which, when purified on silica gel (eluent: chloro-form), gives a further 5.3 g of 4'-bromomethyl-2-cyanobiphenyl and 12.2 g of the expected 3-[(2'-cyanobiphenyl-4-yl)methyl]-2,4-dioxopentane in the form of a yellow oil.

EXAMPLE 15

5-[(2'-Cyanobiphenyl-4-yl)methyl]-4,6-dioxononane

Formula (V): R'$_1$ = CH$_2$—CH$_2$—CH$_3$, V = 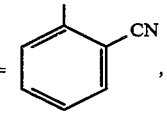, R$_8$ = CH$_2$—CH$_2$—CH$_3$ 15.6 g of 4,6-dioxononane, prepared from methyl propyl ketone and ethyl butyrate in the presence of lithium amide (according to CA 42: 4129 f), are dissolved in 160 ml of anhydrous DMF. 4 g of 60% NaH are added in portions. When the exothermic effect has subsided, the mixture is cooled to room temperature and a solution of 27.2 g of 4'-bromomethyl-2-cyanobiphenyl, prepared in Example 4, in 90 ml of DMF is introduced dropwise. The mixture is stirred for 30 min at room temperature and then heated at 60° C. for 2 h. It is concentrated under vacuum and the concentrate is taken up in a water/dichloromethane mixture and acidified with a dilute solution of HCl. After decantation, the aqueous phase is extracted twice with dichloromethane. The organic phases are washed with water, dried and then concentrated to give 36.3 g of an oil, which is purified by chromatography twice in succession (eluent: chloroform, then cyclohexane 90%/ethyl acetate 10% respectively) to give a solid identified by NMR as being the enol tautomer melting at 105° C., and an oil corresponding to the diketone tautomeric form.

EXAMPLE 16

2,4-Dioxo-3-[(2'-(1H-tetrazol-5-yl)biphenyl-4-yl)methyl]pentane

Formula (V):
R'$_1$=CH$_3$, R$_8$=CH$_3$,

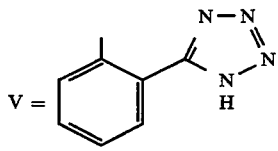

A mixture of 11.8 g of 3-[(2'-cyanobiphenyl-4-yl)methyl]-2,4-dioxopentane, prepared in Example 14, 200 ml of xylene and 9.3 g of trimethyltin azide is refluxed for 50 h. After 24 h, a second equivalent of trimethyltin azide is added.

The mixture is cooled and concentrated to give a viscous oil which, when chromatographed on silica gel (eluent: chloroform 90%/methanol 10%), gives 9.3 g of crystals.

An additional treatment with acetonitrile gives 6.2 g of analytically pure 2,4-dioxo-3-[(2'-(1H-tetrazol-5-yl)biphenyl-4-yl)methyl]pentane.

Empirical formula: $C_{19}H_{18}N_4O_2$.

Melting point: 166° C.

EXAMPLE 17

Ethyl 2-[[2'-(1H-tetrazol-5-yl)biphenyl-4-yl]methyl]-3-oxohexanoate

Formula (V):
$R'_1$=n-propyl, $R_8$=O-ethyl,

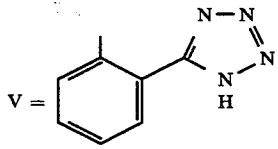

A mixture of 69.9 g of ethyl 2-[(2'-cyanobiphenyl-4-yl)methyl]-3-oxohexanoate, prepared according to Example 5, 700 ml of anhydrous toluene and 47.5 g of trimethyltin azide, prepared from sodium azide and trimethyltin chloride, is refluxed for 24 h. A further 47.5 g of trimethyltin azide are added and reflux is continued for 16 h. The mixture is concentrated to 50%. The orange solution obtained is purified by chromatography twice in succession (eluent: chloroform 90%/methanol 10%, then chloroform 95%/methanol 5%) to give 58 g of an orange oil, which crystallizes.

Melting point: 65° C.

EXAMPLE 18

Method A

6-[(2'-Cyanobiphenyl-4-yl)methyl]-7-hydroxy-5-propyl-1,2,4-triazolo[1,5-a]-pyrimidine Formula (VIIa):
$R'_1$=n-propyl, X=N, Y = CH, $R_{10}$ = OH, V = 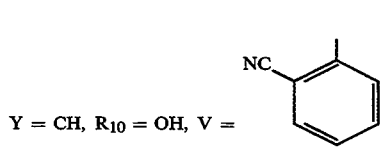

1.7 g of 3-amino-1,2,4-triazole, 7 g of the β-ketoester prepared in Example 5 and 30 ml of acetic acid are refluxed for 6 h. The acetic acid is evaporated off. The oil obtained is purified by chromatography on silica gel (eluent: CHCl₃ 90%/MeOH 10%) to give 5.2 g of the starting β-ketoester and 1.2 g of 6-[(2'-cyanobiphenyl-4-yl)methyl]-7-hydroxy-5-propyl-1,2,4-triazolo[1,5-a]pyrimidine.

Melting point: 200°-205° C.

¹H NMR (200 MHz; DMSO-d₆): 2.65 (t, 2H, propyl CH₂); 8.2 (s, 1H, H₂).

UV (10 μg/ml, MeOH): $\lambda_a$=209.1 nm $\lambda_b$=257.7 nm $\lambda_c$=286.8 nm.

EXAMPLE 19

Method B

6-[(2'-Cyanobiphenyl-4-yl)methyl]-5-hydroxy-7-propyl-1,2,4-triazolo[1,5-a]-pyrimidine Formula (VIIb):
$R'_1$=n-propyl, X=N, Y = CH, $R_{10}$ = OH, V = 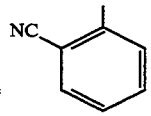

7.1 g of the β-ketoester prepared in Example 5, 1.7 g of 3-amino-1,2,4-triazole and 70 ml of 1,2,4-trichlorobenzene are refluxed for 7 h. The mixture is concentrated under vacuum. The thick oil obtained is chromatographed on silica gel (eluent: CHCl₃ 95%/MeOH 5% to give 0.8 g of the isomer obtained in Example 18 (melting point: 200° C.) and 2.2 g of 6-[(2'-cyanobiphenyl-4-yl)methyl]-5-hydroxy-7-propyl-1,2,4-triazolo-[1,5-a]pyrimidine.

Melting point: 212° C.

¹H NMR (DMSO-d₆): 2.98 (t, 2H, propyl CH₂); 8.1 (s, 1H, H₂).

UV (10 μg/ml, MeOH): $\lambda_a$=207.5 nm $\lambda_b$=258.2 nm.

EXAMPLE 20

Method C

6-[(2'-Cyanobiphenyl-4-yl)methyl]-5-hydroxy-7-propyl-1,2,4-triazolo[4,3-a]-pyrimidine Formula (VIIa):
$R'_1$=n-propyl, X=CH, Y = N, $R_{10}$ = OH, V = 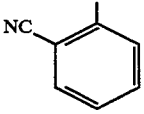

a)

5-[(2'-Cyanobiphenyl-4-yl)methyl]-4-hydroxy-6-propyl-2-mercaptopyrimidine 11 g of thiourea are added with a spatula to a solution of sodium methylate prepared from 4.6 g of sodium and 150 ml of methanol. 34.9 g of the β-ketoester prepared in Example 5, dissolved in 50 ml of methanol, are then introduced dropwise. The mixture is left to stand overnight and then refluxed for 7 h. It is concentrated under vacuum and the concentrate is taken up in 500 ml of water and then acidified with concentrated HCl to bring the pH to 1. The gummy precipitate is isolated and taken up in methanol to give 17.3 g of white crystals of 5-[(2'-cyanobiphenyl-4-yl)methyl]-4-hydroxy-6-propyl-2-mercaptopyrimidine.

Melting point: 196° C.

b) 5-[(2'-Cyanobiphenyl-4-yl)methyl]-4-hydroxy-2-methylmercapto-6-propylpyrimidine Formula (XI): R₁ = n-propyl, V = 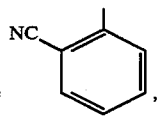,
R₂ = OH 17.3 g of the compound obtained above are introduced in portions into a mixture of 340 ml of methanol and 2.9 g of KOH. After a clear solution has formed, it is cooled and 3.4 ml of ICH₃ are then introduced dropwise.

The mixture is left to react for 2 h at room temperature.

The precipitate is filtered off to give 17.2 g of 5-[(2'-cyanobiphenyl-4-yl)methyl]-4-hydroxy-2-methylmercapto-6-propylpyrimidine.

Melting point: 220° C.

c) 5-[(2'-Cyanobiphenyl-4-yl)methyl]-2-hydrazino-4-hydroxy-6-propylpyrimidine Formula (X): R₁ = n-propyl, V = 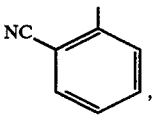,
R₂ = OH 12.4 g of 5-[(2'-cyanobiphenyl-4-yl)methyl]-4-hydroxy-2-methylmercapto-6-propylpyrimidine, prepared above, are dissolved in 370 ml of 2-methoxyethanol. 33 ml of hydrazine hydrate are introduced and the mixture is then refluxed for 3 h. It is concentrated under vacuum and the concentrate is taken up in acetonitrile and triturated. The solid obtained is filtered off and washed with ether and isopropyl ether to give 9.9 g of 5-[(2'-cyanobiphenyl-4-yl)methyl]-2-hydrazino-4-hydroxy-6-propylpyrimidine.

Melting point: 191° C.

d) 6-[(2'-Cyanobiphenyl-4-yl)methyl]-5-hydroxy-7-propyl-1,2,4-triazolo[4,3-a]-pyrimidine Formula (VIIa):
R'₁ = n-propyl, X = CH, Y = N, R₁₀ = OH, V = 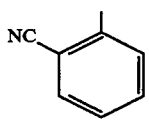

10 g of 5-[(2'-cyanobiphenyl-4-yl)methyl]-2-hydrazino-4-hydroxy-6-propylpyrimidine, prepared as above, are placed in 100 ml of formic acid. The mixture is refluxed for 4 h. It is concentrated under reduced pressure and the thick oil obtained is taken up in water and triturated until it crystallizes.

The compound is purified by chromatography on silica gel (eluent: CHCl₃ 95%/methanol 5%).

This gives 8.3 g of 6-[(2'-cyanobiphenyl-4-yl)methyl]-5-hydroxy-7-propyl-1,2,4-triazolo[4,3-a]-pyrimidine.

Melting point: 217° C.

¹H NMR (DMSO-d₆): 2.6 (t, 2H, propyl CH₂); 9 (s, 1H, H₃).

UV (10 μg/ml, MeOH): λ$_a$=210.2 nm λ$_b$=257.5 nm λ$_c$=303.4 nm.

EXAMPLE 21

6-[(2'-Cyanobiphenyl-4-yl)methyl]-7-hydroxy-5-propyl-1,2,4-triazolo[4,3-a]-pyrimidine Formula (VIIb):
R'₁ = n-propyl, X = CH, Y = N, R₁₀ = OH, V = 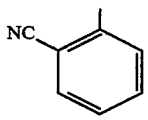

Following the procedure of Example 20, step d), 1.1 g of 6-[(2'-cyanobiphenyl-4-yl)methyl]-7-hydroxy-5-propyl-1,2,4-triazolo[4,3-a]pyrimidine are obtained at the same time as the compound described above.

Melting point: 204°–206° C.

¹H NMR (DMSO-d₆): 2.9 (t, 2H, propyl CH₂); 9 (s, 1H, H₃).

UV (10 μg/ml, MeOH): λ$_a$=211.5 nm λ$_b$=260 nm.

The compounds of Examples 20 and 21 can also be obtained by reacting compound 20 c) with triethyl orthoformate under reflux for 5 h. In this case, the proportion of the compound of Example 21 is found to be slightly improved.

EXAMPLE 22

Method D

6-[(2'-Cyanobiphenyl-4-yl)methyl]-7-hydroxy-5-propyl-1,2,4-triazolo[1,5-a]-pyrimidine Formula (VIIa):
R'₁ = n-propyl, X = N, Y = CH, R₁₀ = OH, V = 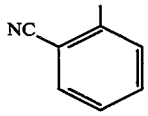

500 mg of 6-[(2'-cyanobiphenyl-4-yl)methyl]-5-hydroxy-7-propyl-1,2,4-triazolo[4,3-a]pyrimidine, prepared in Example 20 d), are heated in a metal bath at 5° C. for 2 h 30 min. It is left to cool and taken up in methanol and then in isopropyl acetate to give 300 mg of cream-colored crystals identical to the compound of Example 18.

Melting point: 200° C.

EXAMPLE 23

Method E

6-[(2'-Cyanobiphenyl-4-yl)methyl]-5-hydroxy-7-propyl-1,2,4-triazolo[1,5-a]-pyrimidine Formula (VIIb):
R'₁ = n-propyl, X = N, Y = CH, R$_{10}$ = OH, V = 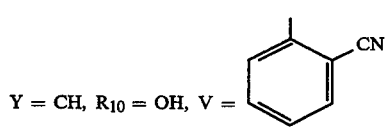

A mixture of 24 g of 3-amino-1,2,4-triazole and 200 g of 5-ethyl-2-methylpyridine is heated to 175° C. 100 g of the β-ketoester prepared in Example 5, dissolved in 100 ml of 5-ethyl-2-methylpyridine, are introduced dropwise. The reaction is left to proceed for 6 h at 175° C. The ethylmethylpyridine is distilled off under vacuum and the residue is taken up in a mixture of water and chloroform. After decantation, the aqueous phase is extracted with chloroform. The combined organic phases are washed with a dilute solution of HCl and then with water, dried and concentrated to give an oil, which crystallizes when triturated in methanol. Recrystallization from n-butanol gives 35.2 g of cream-colored crystals of 6-[(2'-cyanobiphenyl-4-yl)methyl]-5-hydroxy-7-propyl-1,2,4-triazolo[1,5-a]pyrimidine.

Melting point: 210° C.

Purification of the mother liquors by chromatography on silica gel gives a second crop of 6.9 g of the expected compound, together with 13.9 g of the derivative 6-[(2'-cyanobiphenyl-4-yl)methyl]-7-hydroxy-5-propyl-1,2,4-triazolo[1,5-a]pyrimidine obtained in Example 18.

Melting point: 196° C.

The yield of the reaction can be improved by about 10% by adding 10.5 g of 4-dimethylaminopyridine to the initial mixture.

EXAMPLE 24

6-[(2'-Cyanobiphenyl-4-yl)methyl]-7-hydroxy-2-methyl-5-propyl-1,2,4-triazolo-[1,5-a]pyrimidine hydrochloride hemihydrate Formula (VIIa):
R'$_1$=n-propyl, X=N, Y=C-CH$_3$, R$_{10}$=OH, V = 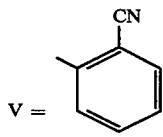

A suspension of 10 g of compound 20 c) in 100 ml of phenyl acetate is refluxed for 4 h. It is concentrated under reduced pressure. The concentrate is taken up in water and extracted with chloroform and the extract is dried and evaporated to give 9.8 g of white crystals melting at 205° C. These crystals are taken up in 50 ml of acetonitrile and 40 ml of a 10% solution of hydrochloric acid in ether to give 7.5 g of 6-[(2'-cyanobiphenyl-4-yl)methyl]-7-hydroxy-2-methyl-5-propyl-1,2,4-triazolo[1,5-a]pyrimidine hydrochloride.

Empirical formula: C$_{23}$H$_{21}$N$_5$O.HCl.½H$_2$O.

Melting point: 190° C.

$^1$H NMR (DMSO-d$_6$): 2.65 (t, 2H, propyl CH$_2$).

UV (MeOH): λ$_a$=213.7 nm λ$_b$=257.7 nm λ$_c$=285 nm.

EXAMPLE 25

6-[(2'-Cyanobiphenyl-4-yl)methyl]-5-hydroxy-7-propyl-3-mercapto-1,2,4-triazolo-[4,3-a]pyrimidine Formula (VIIa):
R'$_1$=n-propyl, X=C-SH, Y=N, R$_{10}$=OH, V = 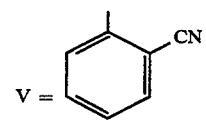

5.3 ml of carbon disulfide are added to a suspension of 10 g of the compound prepared in Example 20 c) in 300 ml of butanol. The mixture is refluxed for 2 h. A further 5.3 ml of CS are added and reflux is then continued for 5 h. The mixture is concentrated under vacuum. The concentrate is taken up in water and extracted 3 times with chloroform. The solvent is evaporated off to give 10.8 g of amorphous crystals, which are purified by chromatography on silica gel (eluent: CHCl$_3$ 90%/MeOH 10%).

A first compound weighing 1.9 g is isolated and identified as 6-[(2'-cyanobiphenyl-4-yl)methyl]-7-hydroxy-5-propyl-3-mercapto-1,2,4-triazolo[4,3-a]pyrimidine. This constitutes the product of Example 25 bis.

Melting point: 240° C.

$^1$H NMR (DMSO-d$_6$): 3.5 (t, 2H, propyl CH$_2$).

A second compound weighing 1 g is the expected product, namely 6-[(2'-cyanobiphenyl-4-yl)methyl]-5-hydroxy-7-propyl-3-mercapto-1,2,4-triazolo[4,3-a]pyrimidine.

Melting point: 180° C.

$^1$H NMR (DMSO-d$_6$): 2.5 (m, propyl CH$_2$+DMSO-d$_6$).

The third product weighing 6.2 g is the starting hydrazino compound 20 c).

EXAMPLE 26

6-[(2'-Cyanobiphenyl-4-yl)methyl]-3,5-dihydroxy-7-propyl-1,2,4-triazolo[4,3-a]-pyrimidine Formula (VIIa):
R'$_1$=n-propyl, X=C-OH, Y=N, R$_{10}$=OH, V = 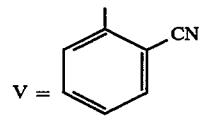

4.6 g of carbonyldiimidazole are added to a mixture of 10 g of the compound prepared in Example 20 c) and 500 ml of THF, heated to 50° C. The whole is refluxed for 7 h and concentrated under vacuum. The concentrate is taken up in water and extracted three times with chloroform. Evaporation of the solvent gives 12.4 g of amorphous crystals, which are purified by chromatography on silica gel (eluent: CHCl$_3$ 95%/MeOH 5%).

A first compound weighing 3.1 g is isolated and identified as 6-[(2'-cyanobiphenyl-4-yl)methyl]-3,7-dihydroxy-5-propyl-1,2,4-triazolo[4,3-a]pyrimidine. This constitutes the product of Example 26 bis.

Melting point: 228° C.

$^1$H NMR (DMSO-d$_6$): 3 (t, 2H, propyl CH$_2$).

The second compound weighing 3.8 g is the expected product, namely 6-[(2'-cyanobiphenyl-4-yl)methyl]-3,5-dihydroxy-7-propyl-1,2,4-triazolo[4,3-a]-pyrimidine.

Melting point: 210° C.

$^1$H NMR (DMSO-d$_6$): 2.4 (t, 2H, propyl CH$_2$).

Using one of the methods described in Examples 19 or 23 (method B or method E), the appropriate aminotriazoles are reacted with the β-ketoesters prepared in Examples 5 to 15 to give the following compounds of Examples 27 to 43.

EXAMPLE 27

6-[(2'-Cyanobiphenyl-4-yl)methyl]-5-hydroxy-2-methyl-7-propyl-1,2,4-triazolo-[1,5-a]pyrimidine Formula (VIIb):
R'$_1$=n-propyl, X=N, Y=C-CH$_3$, R$_{10}$=OH,

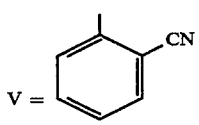

Crystallization from methanol. The mother liquors are purified by chromatography on silica gel (eluent: CHCl$_3$ 95%/MeOH 5%).

Melting point: 218°–220° C.

A second compound is isolated and identified as 6-[(2'-cyanobiphenyl-4-yl)methyl]-7-hydroxy-2-methyl-5-propyl-1,2,4-triazolo[1,5-a]pyrimidine. This constitutes the product of Example 27 bis.

Formula (VIIa):
R'$_1$=n-propyl, X=N, Y=C-CH$_3$, R$_{10}$=OH,

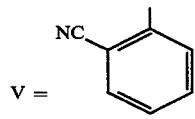

Melting point: 204°–206° C.

EXAMPLE 28

6-[(2'-Cyanobiphenyl-4-yl)methyl]-2-ethyl-5-hydroxy-7-propyl-1,2,4-triazolo[1,5-a]-pyrimidine Formula (VIIb):
R'$_1$=n-propyl, X=N, Y=C-CH$_2$CH$_3$, R$_{10}$=OH,

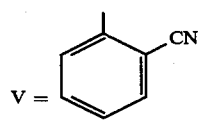

Crystallization from methanol. The mother liquors are purified by chromatography on silica gel (eluent: CHCl$_3$ 95%/MeOH 5%).

Melting point: 216° C.

A second compound is isolated and identified as 6-[(2'-cyanobiphenyl-4-yl)methyl]-2-ethyl-7-hydroxy-5-propyl-1,2,4-triazolo[1,5-a]pyrimidine. This constitutes the product of Example 28 bis.

Formula (VIIa):
R'$_1$=n-propyl, X=N, Y=C-CH$_2$CH$_3$, R$_{10}$=OH,

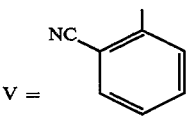

Melting point: 186° C.

EXAMPLE 29

6-[(2'-Cyanobiphenyl-4-yl)methyl]-7-n-butyl-5-hydroxy-1,2,4-triazolo[1,5-a]pyrimidine Formula (VIIb):
R'$_1$=n-butyl, X=N, Y=CH, R$_{10}$=OH,

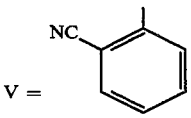

Purified by recrystallization from n-butanol.
Melting point: 210° C.

EXAMPLE 30

2-Amino-6-[(2'-cyanobiphenyl-4-yl)methyl]-5-hydroxy-7-propyl-1,2,4-triazolo[1,5-a]-pyrimidine Formula (VIIb):
R'$_1$=n-propyl, X=N, Y=C-NH$_2$, R$_{10}$=OH,

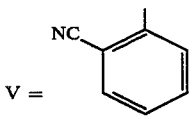

Crystallization from a methanol/chloroform mixture.
Purification of the mother liquors by chromatography on silica gel (eluent: CHCl$_3$ 90%/MeOH 10%).
Melting point: 260° C.

A second compound is isolated and identified as 2-amino-6-[(2'-cyanobiphenyl-4-yl)methyl]-7-hydroxy-5-propyl-1,2,4-triazolo[1,5-a]pyrimidine. This constitutes the product of Example 30 bis.

Formula (VIIa):
R'$_1$=n-propyl, X=N, Y=C-NH$_2$, R$_{10}$=OH,

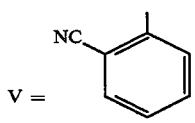

Melting point: 325°–330° C.

EXAMPLE 31

6-[(2'-Cyanobiphenyl-4-yl)methyl]-5-hydroxy-2-methylthio-7-propyl-1,2,4-triazolo[1,5-a]pyrimidine Formula (VIIb):
R'$_1$=n-propyl, X=N, Y=C-SCH$_3$, R$_{10}$=OH,

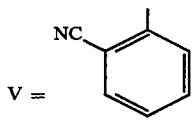

Purification by chromatography on silica gel (eluent: CHCl₃ 95%/MeOH 5%).
Crystallization from isopropyl acetate.
Melting point: 182° C.

EXAMPLE 32

6-[4-(3-Cyano-2-thienyl)benzyl]-5-hydroxy-7-propyl-1,2,4-triazolo[1,5-a]pyrimidine Formula (VIIb):
$R'_1$=n-propyl, X=N, Y=CH, $R_{10}$=OH,

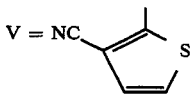

Crystallization from chloroform/water. Purification by recrystallization from 2-methoxyethanol.
Melting point: 246° C.

EXAMPLE 33

6-[4-(3-Cyano-2-pyridyl)benzyl]-5-hydroxy-7-propyl-1,2,4-triazolo[1,5-a]pyrimidine Formula (VIIb):
$R'_1$=n-propyl, X=N, Y=CH, $R_{10}$=OH,

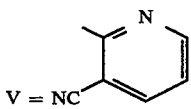

Crystallization from methanol. The mother liquors are purified by chromatography on silica gel (eluent: CH₂Cl₂ 97.5%/MeOH 2.5%). The whole is purified by recrystallization from methanol.
Melting point: 212° C.

EXAMPLE 34

6-[4-(3-Cyano-2-thienyl)benzyl]-5-hydroxy-2-methyl-7-propyl-1,2,4-triazolo[1,5-a]-pyrimidine Formula (VIIb):
$R'_1$=n-propyl, X=N, Y=C-CH₃, $R_{10}$=OH,

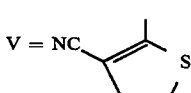

Crystallization from a water/chloroform mixture. Purification by recrystallization from 2-methoxyethanol.
Melting point: 277° C.

EXAMPLE 35

6-[4-(3-Cyano-2-furyl)benzyl]-5-hydroxy-7-propyl-1,2,4-triazolo[1,5-a]pyrimidine Formula (VIIb):
$R'_1$=n-propyl, X=N, Y=CH, $R_{10}$=OH,

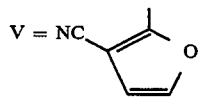

Melting point: 256° C.

EXAMPLE 36

7-Butyl-6-[(2'-cyanobiphenyl-4-yl)methyl]-5-hydroxy-2-methyl-1,2,4-triazolo[1,5-a]-pyrimidine Formula (VIIb):
$R'_1$=n-butyl, X=N, Y=C-CH₃, $R_{10}$=OH,

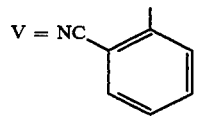

Purified by recrystallization from n-butanol.
Melting point: 230° C.

EXAMPLE 37

6-[(2'-Cyanobiphenyl-4-yl)methyl]-5-hydroxy-2-hydroxymethyl-1,2,4-triazolo[1,5-a]pyrimidine Formula (VIIb):
$R'_1$=n-propyl, X=N, Y=C-CH₂OH, $R_{10}$=OH,

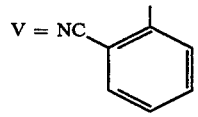

Purification by chromatography on silica gel (eluent: CHCl₃ 95%/MeOH 5%).
Melting point: 214° C.

EXAMPLE 38

6-[(2'-Cyanobiphenyl-4-yl)methyl]-5-hydroxy-7-methoxymethyl-1,2,4-triazolo[1,5-a]pyrimidine Formula (VIIb):
$R'_1$=-CH₂-OCH₃, X=N, Y=CH, $R_{10}$=OH,

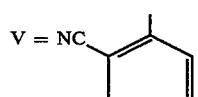

Purified by chromatography on silica gel (eluent: chloroform 95%/methanol 5%).
Melting point: 188° C.

A second compound is isolated and identified as 6-[(2'-cyanobiphenyl-4-yl)methyl]-7-hydroxy-5-methoxymethyl-1,2,4-triazolo[1,5-a]pyrimidine. This constitutes the product of Example 38 bis.

Formula (VIIa):
$R'_1$=-CH₂-OCH₃, X=N, Y=CH, $R_{10}$=OH,

V = NC 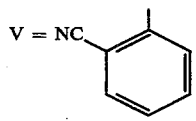

Melting point: 240° C.

EXAMPLE 39

6-[(2'-Cyanobiphenyl-4-yl)methyl]-5-hydroxy-7-methyl-1,2,4-triazolo-[1,5-a]pyrimidine Formula (VIIb):
R'$_1$=CH$_3$, X=N, Y=CH, R$_{10}$ = OH, V = NC 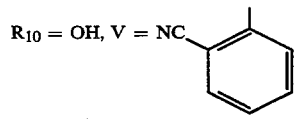

The product is purified by chromatography on silica gel (eluent: CHCl$_3$ 95%/MeOH 5%) and crystallized from methanol.

Melting point: 212° C.

A second compound is isolated and identified as 6-[(2'-cyanobiphenyl-4-yl)methyl]-7-hydroxy-5-methyl-1,2,4-triazolo[1,5-a]pyrimidine. This constitutes the product of Example 39 bis.

Formula (VIIa):
R'$_1$=CH$_3$, X=N, Y=CH,

R$_{10}$ = OH, V = NC 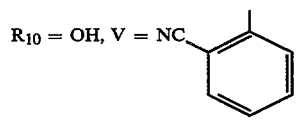

Melting point: 252° C.

EXAMPLE 40

6-[(2'-Cyanobiphenyl-4-yl)methyl]-7-ethyl-5-hydroxy-1,2,4-triazolo[1,5-a]pyrimidine Formula (VIIb):
R'$_1$=ethyl, X=N, Y=CH, R$_{10}$ = OH, V = NC 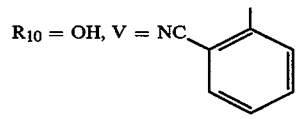

Isolated by chromatography on silica gel (eluent: CHCl$_3$ 95%/MeOH 5%) and purified by recrystallization from n-butanol.

Melting point: 224° C.

A second compound is isolated and identified as 6-[(2'-cyanobiphenyl-4-yl)methyl]-5-ethyl-7-hydroxy-1,2,4-triazolo[1,5-a]pyrimidine. This constitutes the product of Example 40 bis.

Formula (VIIa):
R'$_1$=-CH$_2$-CH$_3$, X=N, Y=CH, R$_{10}$=OH,

V = NC 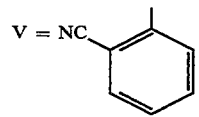

Melting point: 234° C.

EXAMPLE 41

6-[(2'-Cyanobiphenyl-4-yl)methyl]-2-N,N-diethylamino-5-hydroxy-7-propyl-1,2,4-triazolo[1,5-a]pyrimidine Formula (VIIb):
R'$_1$=n-propyl, X=N, Y = C—N , R$_{10}$ = OH, V = NC 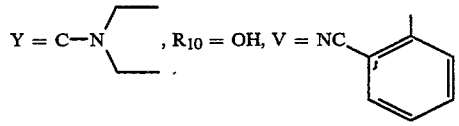

The product is crystallized from methanol.

Melting point: 220° C.

A second compound is isolated in the form of amorphous crystals after chromatography of the mother liquors on silica gel (eluent: CHCl$_3$ 80%/isopropylamine 20%). It is identified as 6-[(2'-cyanobiphenyl-4-yl)methyl]-2-N,N-diethylamino-7-hydroxy-5-propyl-1,2,4-triazolo[1,5-a]pyrimidine. This constitutes the compound of Example 41 bis.

Formula (VIIa):
R'$_1$=n-propyl, X=N,

Y = C—N , R$_{10}$ = OH, V = NC 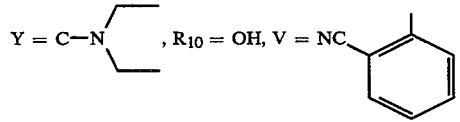

EXAMPLE 42

6-[(2'-Cyanobiphenyl-4-yl)methyl]-5,7-dipropyl-1,2,4-triazolo[1,5-a]pyrimidine

Formula (VIIa):
R'$_1$=n-propyl, X=N, Y=CH, R$_{10}$=n-propyl,

V = NC 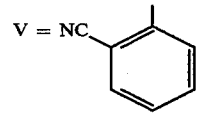

Product purified by chromatography on silica gel (eluent: chloroform 95%/methanol 5%).

Melting point: 160° C.

EXAMPLE 43

7-Benzyloxymethyl-6-[(2'-cyanobiphenyl-4-yl)methyl]-5-hydroxy-1,2,4-triazolo[1,5-a]-pyrimidine Formula (VIIb): R'$_1$ = —CH$_2$—O—CH$_2$— 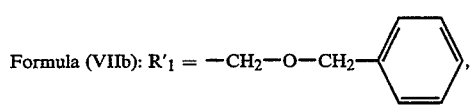

X = N, Y = CH, R$_{10}$ = OH,

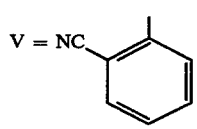

Purified by recrystallization from butanol followed by chromatography on silica gel (eluent: chloroform 95%/methanol 5%).

Melting point: 218° C.

A second compound is isolated and identified as 5-benzyloxymethyl-6-[(2'-cyanobiphenyl-4-yl)methyl]-7-hydroxy-1,2,4-triazolo[1,5-a]pyrimidine. This constitutes the product of Example 43 bis.

Formula (VIIa): R'$_1$ = —CH$_2$—O—CH$_2$—

X = N, Y = CH, R$_{10}$ = OH,

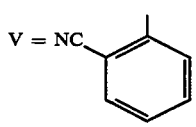

Melting point: 260° C.

EXAMPLE 44

5-Chloro-6-[(2'-cyanobiphenyl-4-yl)methyl]-7-propyl-1,2,4-triazolo[1,5-a]pyrimidine Formula (VIIIb):
R'$_1$=n-propyl, X=N,

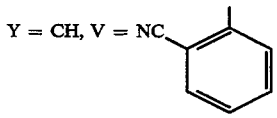

25.9 g of the compound prepared in Example 19 or 23 are added in portions to 260 ml of POCl$_3$. The mixture is refluxed for 4 h. It is concentrated under vacuum, the concentrate is taken up in 200 ml of chloroform stabilized with amylene, and a solution of water and ice is then added. After decantation, the aqueous phase is extracted with chloroform and the organic phases are combined. After washing with water and drying, they are concentrated under vacuum to give a thick oil. The product is crystallized from isopropyl acetate to give 21 g of 5-chloro-6-[(2'-cyanobiphenyl-4-yl)methyl]-7-propyl-1,2,4-triazolo[1,5-a]pyrimidine.

Melting point: 138° C.

The derivative of Example 45 is obtained by the procedure of Example 44 using the derivative prepared in Example 18.

EXAMPLE 45

7-Chloro-6-[(2'-cyanobiphenyl-4-yl)methyl]-5-propyl-1,2,4-triazolo[1,5-a]pyrimidine Formula (VIIIa):
R'$_1$=n-propyl, X=N,

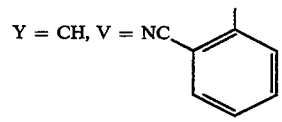

Melting point: 132° C.

EXAMPLE 46

6-[(2'-Cyanobiphenyl-4-yl)methyl]-7-mercapto-5-propyl-1,2,4-triazolo[1,5-a]pyrimidine Formula (IX):
R$_2$=n-propyl, X=N, Y=CH,

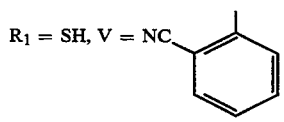

A mixture of 5 g of the chlorinated compound obtained in Example 45, 2 g of thiourea and 150 ml of ethanol is refluxed for 7 h and concentrated under vacuum. The yellow solid is taken up in 60 ml of a 0.5N solution of NaOH. The small amount of insoluble material is filtered off. The filtrate is acidified with acetic acid. The yellow precipitate is filtered off and purified by chromatography on silica gel (eluent: chloroform 90%/methanol 10%) to give 3.4 g of 6-[(2'-cyanobiphenyl-4-yl)methyl]-7-mercapto-5-propyl-1,2,4-triazolo[1,5-a]pyrimidine.

Melting point: 200°–205° C.

EXAMPLE 47

6-[(2'-Cyanobiphenyl-4-yl)methyl]-5-mercapto-7-propyl-1,2,4-triazolo[1,5-a]pyrimidine Formula (IX):
R$_1$=n-propyl, X=N, Y=CH,

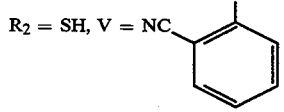

A mixture of 11.1 g of the derivative prepared in Example 19 or Example 23, 350 ml of toluene and 13.4 g of Lawesson's reagent is refluxed for 2 h. The yellow solid obtained is filtered off. Purification by chromatography on silica gel (eluent: CH$_2$Cl$_2$ 90%/acetone 10%) gives 10 g of 6-[(2'-cyanobiphenyl-4-yl)methyl]-5-mercapto-7-propyl-1,2,4-triazolo[1,5-a]pyrimidine.

Melting point: 226° C.

EXAMPLE 48

6-[(2'-Cyanobiphenyl-4-yl)methyl]-7-propyl-1,2,4-triazolo[1,5-a]pyrimidine

Formula (IX):
R$_1$=n-propyl, X=N, Y=CH, $R_2 = H$, $V = NC$— 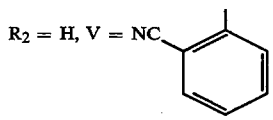

A solution of 5.4 g of the compound prepared in Example 44 in 110 ml of 2-methoxyethanol containing 1.2 g of anhydrous sodium acetate is hydrogenated at atmospheric pressure and room temperature in the presence of 1.4 g of 5% Pd-on-charcoal. The system is purged with nitrogen. The catalyst is filtered off on Célite 545 and washed with hot 2-methoxyethanol. The filtrate is concentrated and the crystals obtained are taken up in ether to give 3.7 g of crude product. Purification by chromatography on silica gel (eluent: dichloromethane 90%/acetone 10%) gives 2.5 g of white crystals of 6-[(2'-cyanobiphenyl-4-yl)methyl]-7-propyl-1,2,4-triazolo[1,5-a]pyrimidine.

Melting point: 180° C.

EXAMPLE 49

6-[(2'-Cyanobiphenyl-4-yl)methyl]-5-methoxy-7-propyl-1,2,4-triazolo[1,5-a]pyrimidine Formula (IX):
$R_1$=n-propyl, X=N, Y=CH, $R_2 = OCH_3$, $V = NC$— 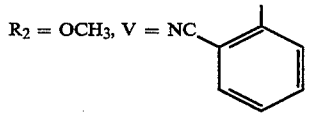

A solution of sodium methylate, prepared from 0.8 g of sodium and 25 ml of methanol, is added to a solution of 11.6 g of the compound of Example 44 in 120 ml of 1,2-dimethoxyethane. The mixture is stirred at room temperature for 3 h. The insoluble material is filtered off and the filtrate is concentrated. The crystals obtained are taken up in water, filtered off and washed firstly with water and then with isopropyl alcohol and ether to give 9.5 g of 6-[(2'-cyanobiphenyl-4-yl)methyl]-5-methoxy-7-propyl-1,2,4-triazolo-[1,5-a]pyrimidine.

Melting point: 166° C.

EXAMPLE 50

Ethyl [6-[(2'-cyanobiphenyl-4-yl)methyl]-7-propyl-1,2,4-triazolo[1,5-a]pyrimidin-5-yl]mercaptoacetate Formula (IX):
$R_1$=n-propyl, X=N, Y=CH, $R_2$=-S-CH$_2$-COOCH$_2$-CH$_3$, $V = NC$— 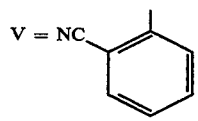

0.6 g of 60% NaH is added in portions to a solution of 1.8 g of ethyl mercaptoacetate in 50 ml of toluene. The mixture is maintained at a temperature of 40° for ½ h and then cooled to room temperature. A solution of 5 g of the compound prepared in Example 44 in 50 ml of anhydrous toluene is then introduced. The reaction is left to proceed at room temperature for 3 h and then at 50° C. for 4 h. A second equivalent of the sodium salt of ethyl mercaptoacetate, prepared as above, is added to complete the reaction. After hydrolysis and decantation, the organic phase is washed with water and then with a dilute solution of acetic acid, dried and concentrated. The oil obtained is purified by chromatography on silica gel (eluent: dichloromethane 90%/acetone 10%) to give 5.4 g of ethyl [6-[(2'-cyanobiphenyl-4-yl)methyl]-7-propyl-1,2,4-triazolo[1,5-a]pyrimidin-5-yl]mercaptoacetate.

Melting point: 76° C.

The compound of Example 51 is obtained by the procedure of Example 50 using 2-methoxyethanol instead of ethyl mercaptoacetate.

EXAMPLE 51

[6-[(2'-Cyanobiphenyl-4-yl)methyl]-7-propyl-1,2,4-triazolo[1,5-a]pyrimidin-5-yl]2-methoxyethyl ether Formula (IX):
$R_1$=n-propyl, X=N, Y=CH, $R_2$=-O-CH$_2$-CH$_2$-OCH$_3$, $V = NC$— 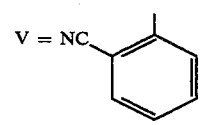

Product crystallized from isopropyl ether.
Melting point: 102° C.

EXAMPLE 52

5-Amino-6-[(2'-cyanobiphenyl-4-yl)methyl]-7-propyl-1,2,4-triazolo[1,5-a]pyrimidine Formula (IX):
$R_1$=n-propyl, X=N, Y=CH, $R_2 = NH_2$, $V = NC$— 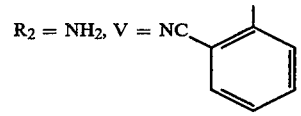

A mixture of 10 g of the derivative prepared in Example 44 and 200 ml of a soluton of 1,2-dimethoxyethane saturated with ammonia is placed in an autoclave. It is heated at 125° C. for 24 h and taken up in a chloroform/water mixture. After decantation, the aqueous phase is extracted. The organic phases are combined, dried and concentrated to give 8.1 g of 5-amino-6-[(2'-cyanobiphenyl-4-yl)methyl]-7-propyl-1,2,4-triazolo[1,5-a]pyrimidine.

Melting point: 206° C.

EXAMPLE 53

6-[(2'-Cyanobiphenyl-4-yl)methyl]-7-N,N-diethylamino-5-propyl-1,2,4-triazolo-[1,5-a]pyrimidine Formula (IX):
$R_2$=n-propyl, X=N, Y=CH,

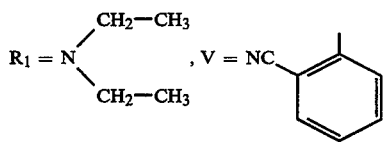

A mixture of 5 g of the chlorinated derivative of Example 45, 100 ml of ethanol, 16 ml of diethylamine and 1.5 g of sodium carbonate is refluxed for 4 h. It is concentrated under vacuum and the thick oil is taken up in water. It is extracted three times with dichloromethane and the extracts are dried and concentrated. The compound obtained is purified by chromatography on silica gel (eluent: chloroform 95%/methanol 5%) to give 5 g of 6-[(2'-cyanobiphenyl-4-yl)methyl]-7-N,N-diethylamino-5-propyl-1,2,4-triazolo[1,5-a]pyrimidine in the form of an orange oil.

The following compounds of Examples 54 to 58 are obtained by reacting one of the derivatives described in Examples 44 or 45 with appropriate amines by either one of the two methods described in Examples 52 and 53.

EXAMPLE 54

6-[(2'-Cyanobiphenyl-4-yl)methyl]-5-N,N-diethylamino-7-propyl-1,2,4-triazolo-[1,5-a]pyrimidine Formula (IX):
$R_1$=n-propyl, X=N, Y=CH,

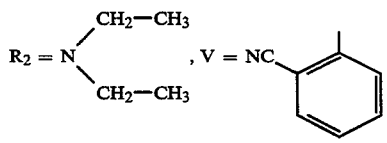

Product crystallized from hot isopropyl ether.
Melting point: 133° C.

EXAMPLE 55

6-[(2'-Cyanobiphenyl-4-yl)methyl]-7-propyl-5-(pyrrolidin-1-yl)-1,2,4-triazolo[1,5-a]-pyrimidine Formula (IX):
$R_1$=n-propyl, X=N, Y=CH,

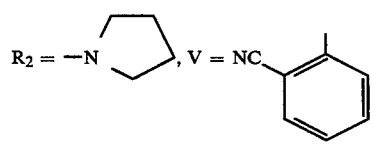

Product crystallized from hot isopropyl ether.
Melting point: 166° C.

EXAMPLE 56

6-[(2'-Cyanobiphenyl-4-yl)methyl]-7-propyl-5-(morpholin-4-ylethylamino)-1,2,4-triazolo[1,5-a]pyrimidine Formula (IX):
$R_1$=n-propyl, X=N, Y=CH,

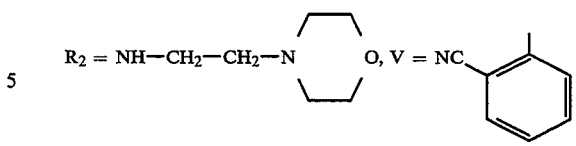

Oily product purified by chromatography on silica gel (eluent: chloroform 95%/methanol 5%).

EXAMPLE 57

6-[(2'-Cyanobiphenyl-4-yl)methyl]-5-(piperidin-1-yl)-7-propyl-1,2,4-triazolo[1,5-a]-pyrimidine Formula (IX):
$R_1$=n-propyl, X=N, Y=CH,

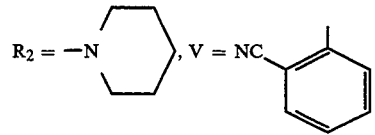

Compound purified by recrystallization from 2-methoxyethanol.
Melting point: 266° C.

EXAMPLE 58

6-[(2'-Cyanobiphenyl-4-yl)methyl]-5-hydrazino-7-propyl-1,2,4-triazolo[1,5-a]pyrimidine Formula (IX):
$R_1$=n-propyl, X=N, Y=CH,

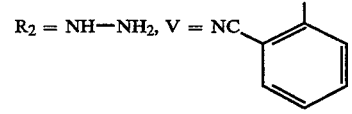

Product crystallized from ether.
Melting point: 161° C.

EXAMPLE 59

5-Azido-6-[(2'-cyanobiphenyl-4-yl)methyl]-7-propyl-1,2,4-triazolo[1,5-a]pyrimidine Formula (IX):
$R_1$=n-propyl, X=N, Y=CH,

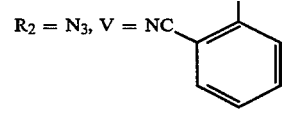

10.3 g of the compound prepared in Example 58, 2.3 ml of concentrated HCl and 300 ml of acetic acid are mixed. A solution of 1.9 g of NaNO$_2$ in 20 ml of water is added. The mixture is left overnight at room temperature. Water is added and the mixture is decanted and extracted with ethyl acetate. The organic phases are combined, washed with water, dried and evaporated. Purification by chromatography twice in succession (eluent: dichloromethane 95%/methanol 5% and dichloromethane 90%/methanol 10%) gives 4.3 g of 5- azido-6-[(2'-cyanobiphenyl-4-yl)methyl]-7-propyl-1,2,4-triazolo[1,5-a]pyrimidine.

Melting point: 134° C.

This same compound can be considered as a tricyclic derivative according to the known equilibrium of azides in the 2-position of nitrogen-containing rings (cf. Temple and Montgomery, J. Org. Chem., 30, 826 (1965)).

EXAMPLE 60

3-Amino-5-hydroxymethyl-1,2,4-triazole

Formula (II):
$R_7 = -CH_2OH$

A mixture of 136 g of aminoguanidine bicarbonate and 80 g of glycolic acid is heated gradually to 120° C. The reaction is continued for 5 h at this temperature. The mixture is taken up in 100 ml of ethanol and the solid is filtered off to give 45.7 g of 3-amino-5-hydroxymethyl-1,2,4-triazole.

Melting point: 192°–194° C.

EXAMPLE 61

3-Amino-5-N,N-diethylamino-1,2,4-triazole

Formula (II):

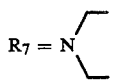

10.3 ml of diethylamine are added to a solution of 16.1 g of dimethyl N-cyanodithioiminocarbonate in 160 ml of acetonitrile. The mixture is stirred for one hour at room temperature and then refluxed until no more methylmercaptan is evolved. The solution is cooled with an ice bath and 5 ml of hydrazine hydrate are introduced. The mixture is refluxed for 4 h. After distillation of the solvent, the product is taken up in acetonitrile to give 8.9 g of white crystals of 3-amino-5-N,N-diethylamino-1,2,4-triazole.

Melting point: 134° C.

EXAMPLE 62

7-Hydroxy-5-propyl-6-[(2'-(1H-tetrazol-5-yl)biphenyl-4-yl)methyl]-1,2,4-triazolo-[1,5-a]pyrimidine Formula (I):
$R_1 = OH$, $R_2 = n$-propyl, $X = N$,

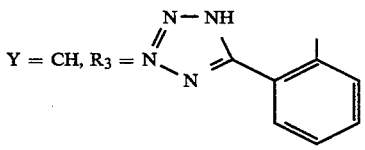

A mixture of 7.8 g of the β-ketoester of Example 17, 1.7 g of 3-amino-1,2,4-triazole and 70 ml of 1,2,4-trichlorobenzene is heated at 120° C. for 7 h. The precipitate obtained is purified by chromatography on silica gel (eluent: $CH_2Cl_2$ 80%/methanol 20%). The compound obtained is dissolved in a 1N solution of NaOH, the insoluble material is filtered off and the clear solution is acidified by bubbling $SO_2$ to give 2.4 g of a white precipitate of 7-hydroxy-5-propyl-6-[(2'-(1H-tetrazol-5-yl)biphenyl-4-yl)methyl]-1,2,4-triazolo[1,5-a]pyrimidine.

Empirical formula: $C_{22}H_{20}N_8O.0.5H_2O$.

Melting point: 260°–265° C. with decomposition.

$^1$H NMR (DMSO-d$_6$): 2.6 (t, 2H, propyl $CH_2$); 8.2 (s, 1H, H$_2$).

UV (MeOH): $\lambda_a = 210$ nm $\lambda_b = 250$ nm.

EXAMPLE 63

5-Hydroxy-7-propyl-6-[(2'-(1H-tetrazol-5-yl)biphenyl-4-yl)methyl]-1,2,4-triazolo-[1,5-a]pyrimidine Formula (I):
$R_1 = n$-propyl, $R_2 = OH$, $X = N$,

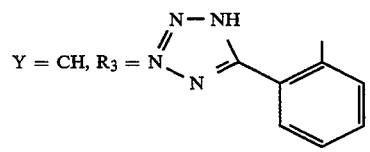

A mixture of 25 g of the compound obtained according to Example 19 or 23, 750 ml of xylene and 34.5 g of trimethyltin azide is refluxed for 50 h. The white precipitate obtained is filtered off. It melts at 290° C. with decomposition. This compound is suspended in 500 ml of THF. Gaseous hydrochloric acid is bubbled in for 30 min to give a total solution, which is then concentrated under vacuum. The concentrate is taken up in water and triturated. The gum obtained is crystallized from acetonitrile. Recrystallization from isopropanol gives 15.2 g of the expected derivative.

Melting point: 242° C.

The mother liquors are concentrated, the concentrate is rendered basic with a 1N solution of KOH and extraction is carried out with chloroform, followed by neutralization with acetic acid. The precipitate obtained is recrystallized twice from isopropanol to give 4.5 g of a second crop of the compound 5-hydroxy-7-propyl-6-[(2'-(1H-tetrazol-5-yl)-biphenyl-4-yl)methyl]-1,2,4-triazolo[1,5-a]pyrimidine.

Empirical formula: $C_{22}H_{20}N_8O$.

Melting point: 242°–244° C.

$^1$H NMR (DMSO-d$_6$): 2.91 (t, 2H, propyl $CH_2$); 8.11 (s, 1H, H$_2$).

The following compounds of Examples 64 to 95 were prepared by one or other of the procedures described in Examples 62 and 63.

EXAMPLE 64

7-Hydroxy-2-methyl-5-propyl-6-[(2'-(1H-tetrazol-5-yl)biphenyl-4-yl)methyl]-1,2,4-triazolo[1,5-a]pyrimidine hemisulfate Formula (I):
$R_1 = OH$, $R_2 = n$-propyl, $X = N$,

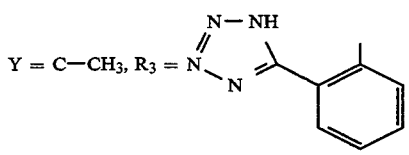

Empirical formula: $C_{23}H_{22}N_8O.0.5H_2SO_4$.

Melting point: 236°–238° C.

$^1$H NMR (DMSO-d$_6$): 2.6 (t, 2H, propyl $CH_2$).

UV (MeOH): $\lambda_a = 212.1$ nm $\lambda_b = 250$ nm.

EXAMPLE 65

5-Hydroxy-7-propyl-6-[(2'-(1H-tetrazol-5-yl)biphenyl-4-yl)methyl]-1,2,4-triazolo-[4,3-a]pyrimidine Formula (I):
$R_1$=OH, $R_2$=n-propyl, X=CH, Y=N,

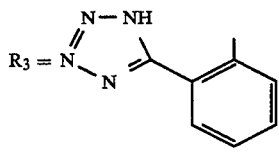

Empirical formula: $C_{22}H_{20}N_8O$.
Melting point: 251° C.
$^1$H NMR (DMSO-$d_6$): 2.55 (t, 2H, propyl $CH_2$); 9 (s, 1H, $H_3$).

EXAMPLE 66

5-Propyl-7-mercapto-6-[(2'-(1H-tetrazol-5-yl)biphenyl-4-yl)methyl]-1,2,4-triazolo-[1,5-a]pyrimidine Formula (I):
$R_1$=SH, $R_2$=n-propyl, X=N,

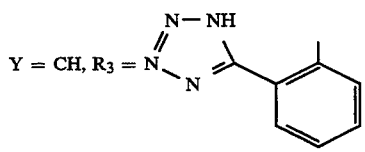

Empirical formula: $C_{22}H_{20}N_8S$.
Melting point: 288° C.
$^1$H NMR (DMSO-$d_6$): 2.59 (t, 2H, n-propyl $CH_2$); 8.6 (s, 1H, $H_2$).

EXAMPLE 67

5,7-Dimethyl-6-[(2'-(1H-tetrazol-5-yl)-biphenyl-4-yl)methyl]-1,2,4-triazolo-[1,5-a]pyrimidine Formula (I):
$R_1$=$CH_3$, $R_2$=$CH_3$, X=N,

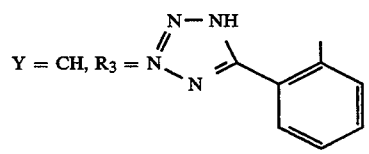

This compound was obtained by the procedure of Example 62 using the 2,4-dioxo-3-[(2'-(1H-tetrazol-5-yl)biphenyl-4-yl)methyl]pentane prepared in Example 16.

Empirical formula: $C_{21}H_{18}N_8$.
Melting point: 264° C.
$^1$H NMR (DMSO-$d_6$): 2.48 (s, 3H, $CH_3$); 2.81 (s, 3H, $CH_3$); 8.56 (s, 1H, $H_2$).

EXAMPLE 68

2-Ethyl-7-hydroxy-5-propyl-6-[(2'-(1H-tetrazol-5-yl)biphenyl-4-yl)methyl]-1,2,4-triazolo[1,5-a]pyrimidine Formula (I):
$R_1$=OH, $R_2$=n-propyl, X=N,
Y=C-$CH_2$-$CH_3$,

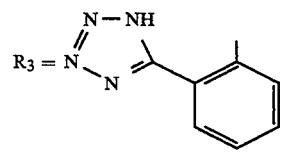

Empirical formula: $C_{24}H_{24}N_8O$.
Melting point: 246° C.
$^1$H NMR (DMSO-$d_6$): 2.57 (m, 2H, propyl $CH_2$+DMSO-$d_6$).

EXAMPLE 69

7-N,N-Diethylamino-5-propyl-6-[(2'-(1H-tetrazol-5-yl)biphenyl-4-yl)methyl]-1,2,4-triazolo[1,5-a]pyrimidine

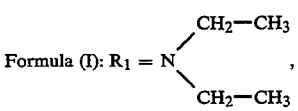

$R_2$ = n-propyl, X = N, Y = CH,

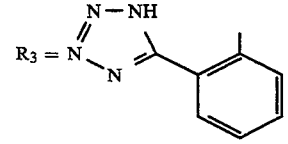

Empirical formula: $C_{25}N_{29}N_5$.
Melting point: 192° C.
$^1$H NMR (DMSO-$d_6$): 2.65 (t, 2H, n-propyl $CH_2$); 8.5 (s, 1H, $H_2$).

EXAMPLE 70

5-Azido-7-propyl-6-[(2'-(1H-tetrazol-5-yl)-biphenyl-4-yl)methyl]-1,2,4-triazolo-[1,5-a]pyrimidine Formula (I):
$R_1$=n-propyl, $R_2$=$N_3$, X=N,

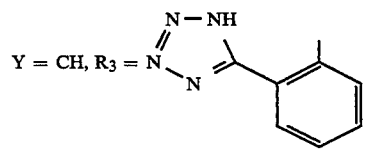

Empirical formula: $C_{22}H_{19}N_{11}$.
Melting point: 212°–213° C.
$^1$H NMR (DMSO-$d_6$): 3.17 (t, 2H, n-propyl $CH_2$); 4.06 (s, 2H, benzyl $CH_2$, azido/tetrazole equilibrium~10%); 4.47 (s, 2H, benzyl $CH_2$); 8.56 (s, 1H, $H_2$, azido/tetrazole equilibrium~10%); 8.7 (s, 1H, $H_2$).

EXAMPLE 71

3,5-Dihydroxy-5-propyl-6-[(2'-(1H-tetrazol-5-yl)biphenyl-4-yl)methyl]-1,2,4-triazolo-[4,3-a]pyrimidine Formula (I):
$R_1$=n-propyl, $R_2$=OH,
X=COH, Y=N,

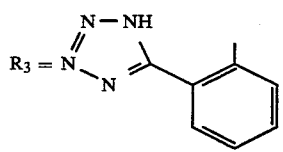

Empirical formula: $C_{22}H_{20}N_8O_2$.
Melting point: 252° C.
$^1H$ NMR (DMSO-$d_6$): 2.93 (t, 2H, n-propyl CH$_2$); 3.7 (s, 2H, benzyl CH$_2$).

EXAMPLE 72

5-Hydroxy-2-methyl-7-propyl-6-[(2'-(1H-tetrazol-5-yl)biphenyl-4-yl)methyl]-1,2,4-triazolo[4,3-a]pyrimidine Formula (I):
$R_1$=n-propyl, $R_2$=OH, X=N,

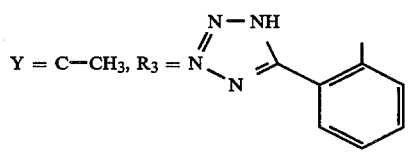

Empirical formula: $C_{23}H_{22}N_8O$.
Melting point: 286° C.
$^1H$ NMR (DMSO-$d_6$): 2.85 (t, 2H, n-propyl CH$_2$); 3.84 (s, 2H, benzyl CH$_2$).

EXAMPLE 73

2-Ethyl-5-hydroxy-7-propyl-6-[(2'-(1H-tetrazol-5-yl)biphenyl-4-yl)methyl]-1,2,4-triazolo[4,3-a]pyrimidine Formula (I):
$R_1$=n-propyl, $R_2$=OH, X=N, Y=C-CH$_2$CH$_3$,

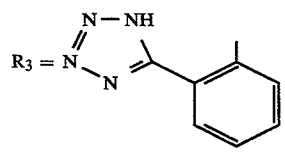

Empirical formula: $C_{24}H_{24}N_8O$.
Melting point: 260° C.
$^1H$ NMR (DMSO-$d_6$): 2.86 (t, 2H, n-propyl CH$_2$); 3.85 (s, 2H, benzyl CH$_2$).

EXAMPLE 74

7-Butyl-5-hydroxy-6-[(2'-(1H-tetrazol-5-yl)biphenyl-4-yl)methyl]-1,2,4-triazolo-[1,5-a]pyrimidine Formula (I):
$R_1$=n-butyl, $R_2$=OH, X=N,

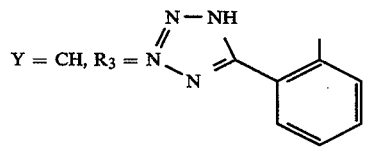

Empirical formula: $C_{23}H_{22}N_8O$.
Melting point: 255° C.

$^1H$ NMR (DMSO-$d_6$): 2.92 (t, 2H, n-propyl CH$_2$); 3.86 (s, 2H, benzyl CH$_2$); 8.11 (s, 1H, H$_2$).

EXAMPLE 75

2-Amino-5-hydroxy-7-propyl-6-[(2'-(1H-tetrazol-5-yl)biphenyl-4-yl)methyl]-1,2,4-triazolo[1,5-a]pyrimidine Formula (I):
$R_1$=n-propyl, $R_2$=OH, X=N,

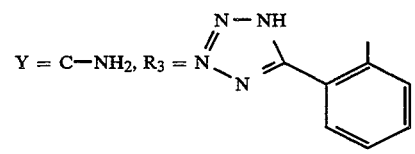

Empirical formula: $C_{22}H_{21}N_9O$.
Melting point: 282° C.
$^1H$ NMR (DMSO-$d_6$): 2.76 (t, 2H, n-propyl CH$_2$); 3.8 (s, 2H, benzyl CH$_2$).

EXAMPLE 76

5-N,N-Diethylamino-7-propyl-6-[(2'-(1H-tetrazol-5-yl)biphenyl-4-yl)methyl]-1,2,4-triazolo[1,5-a]pyrimidine Formula (I):
$R_1$=n-propyl,

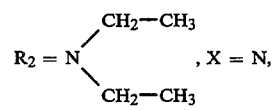

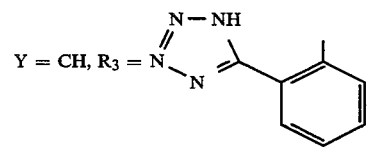

Empirical formula: $C_{26}H_{29}N_9$.
Melting point: 140° C., then 205° C.
$^1H$ NMR (DMSO-$d_6$): 2.91 (t, 2H, propyl CH$_2$); 4.07 (s, 2H, benzyl CH$_2$); 8.32 (s, 1H, H$_2$).

EXAMPLE 77

5-Amino-7-propyl-6-[(2'-(1H-tetrazol-5-yl)-biphenyl-4-yl)methyl]-1,2,4-triazolo-[1,5-a]pyrimidine Formula (I):
$R_1$=n-propyl, $R_2$=-NH$_2$,

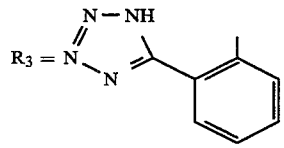

Empirical formula: $C_{22}H_{21}N_9$.
Melting point: 276° C.
$^1H$ NMR (DMSO-$d_6$): 2.98 (t, 2H, propyl CH$_2$); 4.03 (s, 2H, benzyl CH$_2$); 8.1 (s, 1H, H$_2$).

EXAMPLE 78

5-Hydroxy-2-mercaptomethyl-7-propyl-6-[(2'-(1H-tetrazol-5-yl)biphenyl-4-yl)methyl]-1,2,4-triazolo[1,5-a]pyrimidine Formula (I):
$R_1$=n-propyl, $R_2$=OH, X=N,

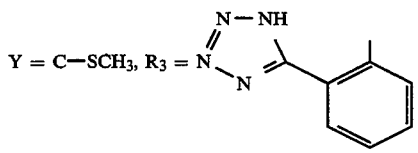

Empirical formula: $C_{23}H_{22}N_8OS$.
Melting point: 260° C.
$^1H$ NMR (DMSO-$d_6$): 2.85 (t, 2H, n-propyl $CH_2$); 3.84 (s, 2H, benzyl $CH_2$).

EXAMPLE 79

5-Hydroxy-7-propyl-6-[4-[3-(1H-tetrazol-5-yl)-2-thienyl]benzyl]-1,2,4-triazolo-[1,5-a]pyrimidine Formula (I):
$R_1$=n-propyl, $R_2$=OH, X=N,

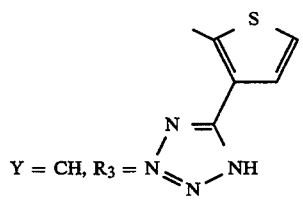

Empirical formula: $C_{20}H_{18}N_8OS$.
Melting point: 275° C.
$^1H$ NMR (DMSO-$d_6$): 2.95 (t, 2H, n-propyl $CH_2$); 3.91 (s, 2H, benzyl $CH_2$); 8.12 (s, 1H, $H_2$).

EXAMPLE 80

5-Hydroxy-7-propyl-6-[4-[3-(1H-tetrazol-5-yl)-2-pyridyl]benzyl]-1,2,4-triazolo-[1,5-a]pyrimidine Formula (I):
$R_1$=n-propyl, $R_2$=OH, X=N,

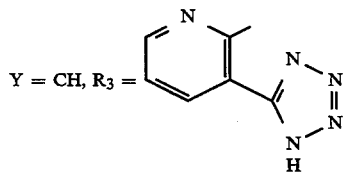

Empirical formula: $C_{21}H_{19}N_9O$.
Melting point: 244° C.
$^1H$ NMR (DMSO-$d_6$): 2.91 (t, 2H, n-propyl $CH_2$); 3.89 (s, 2H, benzyl $CH_2$); 8.11 (s, 1H, $H_2$ with pyridine $H_4$).

EXAMPLE 81

5-Hydroxy-2-methyl-7-propyl-6-[4-[3-(1H-tetrazol-5-yl)-2-thienyl]benzyl]-1,2,4-triazolo[1,5-a]pyrimidine Formula (I):
$R_1$=n-propyl, $R_2$=OH, X=N,

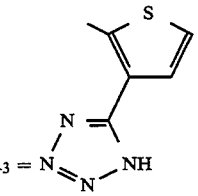

Empirical formula: $C_{21}H_{20}N_8OS$.
Melting point: 287° C.
$^1H$ NMR (DMSO-$d_6$): 2.9 (t, 2H, n-propyl $CH_2$); 3.89 (s, 2H, benzyl $CH_2$).

EXAMPLE 82

7-Butyl-5-hydroxy-2-methyl-6-[(2'-(1H-tetrazol-5-yl)biphenyl-4-yl)methyl]-1,2,4-triazolo[1,5-a]pyrimidine Formula (I):
$R_1$=n-butyl, $R_2$=OH, X=N,

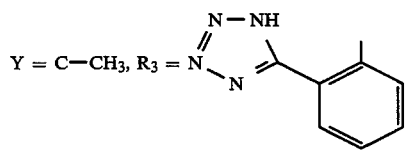

Empirical formula: $C_{24}H_{24}N_8O$.
Melting point: 275° C.
$^1H$ NMR (DMSO-$d_6$): 2.87 (t, 2H, n-butyl $CH_2$); 3.84 (s, 2H, benzyl $CH_2$).

EXAMPLE 83

5-Hydroxy-2-hydroxymethyl-7-propyl-6-[(2'-(1H-tetrazol-5-yl)biphenyl-4-yl)methyl]-1,2,4-triazolo[1,5-a]pyrimidine Formula (I):
$R_1$=n-propyl, $R_2$=OH, X=N,

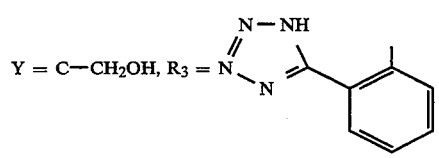

Empirical formula: $C_{23}H_{22}N_8O_2$.
Melting point: 274° C.
$^1H$ NMR (DMSO-$d_6$): 2.88 (t, 2H, n-propyl $CH_2$); 3.86 (s, 2H, benzyl $CH_2$).

EXAMPLE 84

5-Mercapto-7-propyl-6-[(2'-(1H-tetrazol-5-yl)biphenyl-4-yl)methyl]-1,2,4-triazolo-[1,5-a]pyrimidine Formula (I):
$R_1$=n-propyl, $R_2$=SH, X=N

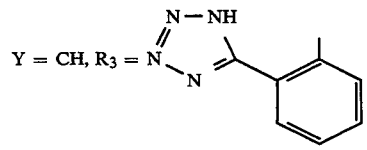

Empirical formula: $C_{22}H_{20}N_8S$.
Melting point: 278° C.
$^1H$ NMR (DMSO-$d_6$): 2.87 (t, 2H, n-propyl $CH_2$); 3.37 (s, 2H, benzyl $CH_2$); 8.29 (s, 1H, $H_2$).

EXAMPLE 85

5-Hydroxy-7-methoxymethyl-6-[(2'-(1H-tetrazol-5-yl)biphenyl-4-yl)methyl]-1,2,4-triazolo[1,5-a]pyrimidine Formula (I):
$R_1 = -CH_2-O-CH_3$; $R_2 = OH$, $X = N$, $Y = CH$,

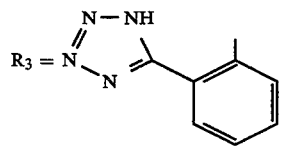

Empirical formula: $C_{21}H_{18}N_8O_2$.
Melting point: 264° C.
$^1H$ NMR (DMSO-$d_6$): 3.91 (t, 2H, benzyl $CH_2$); 4.79 (s, 2H, O-$CH_2$); 8.12 (s, 1H, $H_2$).

EXAMPLE 86

7-Propyl-5-(pyrrolidin-1-yl)-6-[(2'-(1H-tetrazol-5-yl)biphenyl-4-yl)methyl]-1,2,4-triazolo[1,5-a]pyrimidine

X = N, Y = CH,

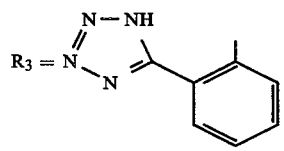

Empirical formula: $C_{26}H_{27}N_9$.
Melting point: 280° C.
$^1H$ NMR (DMSO-$d_6$): 2.94 (t, 2H, propyl $CH_2$); 4.22 (s, 2H, benzyl $CH_2$); 8.18 (s, 1H, $H_2$).

EXAMPLE 87

5-Hydroxy-7-methyl-6-[(2'-(1H-tetrazol-5-yl)biphenyl-4-yl)methyl]-1,2,4-triazolo-[1,5-a]pyrimidine Formula (I):
$R_1 = -CH_3$, $R_2 = OH$, $X = N$,

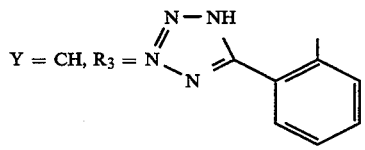

Empirical formula: $C_{20}H_{16}N_8O$.
Melting point: 248° C.
$^1H$ NMR (DMSO-$d_6$): 2.56 (s, 3H, $CH_3$); 3.86 (s, 2H, benzyl $CH_2$); 8.11 (s, 1H, $H_2$).

EXAMPLE 88

7-Ethyl-5-hydroxy-6-[(2'-(1H-tetrazol-5-yl)biphenyl-4-yl)methyl]-1,2,4-triazolo-[1,5-a]pyrimidine Formula (I):
$R_1 = -CH_2-CH_3$, $R_2 = OH$, $X = N$,

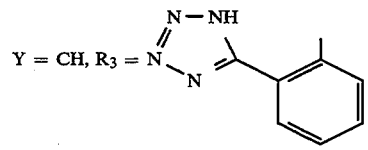

Empirical formula: $C_{21}H_{18}N_8O$.
Melting point: 245° C.
$^1H$ NMR (DMSO-$d_6$): 2.94 (q, 2H, ethyl $CH_2$); 3.87 (s, 2H, benzyl $CH_2$); 8.12 (s, 1H, $H_2$).

EXAMPLE 89

2-N,N-Diethylamino-5-hydroxy-6-[(2'-(1H-tetrazol-5-yl)biphenyl-4-yl)methyl]-1,2,4-triazolo[1,5-a]pyrimidine Formula (I):
$R_1 = $ n-propyl, $R_2 = OH$, $X = N$,

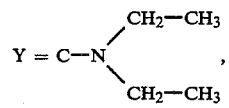

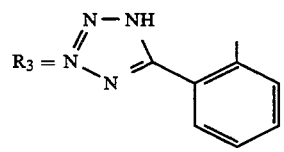

Empirical formula: $C_{26}H_{29}N_9O$.
Melting point: 207° C.
$^1H$ NMR (DMSO-$d_6$): 2.79 (t, 2H, n-propyl $CH_2$); 3.80 (s, 2H, benzyl $CH_2$).

EXAMPLE 90

5-(Morpholin-4-ylethylamino)-7-propyl-6-[(2'-(1H-tetrazol-5-yl)biphenyl-4-yl)-methyl]-1,2,4-triazolo[1,5-a]pyrimidine Formula (I):
$R_1 = $ n-propyl,

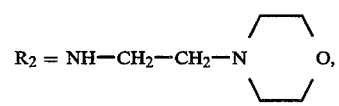

X = N, Y = CH,

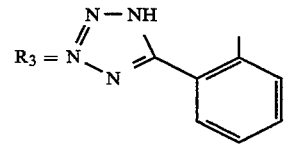

Empirical formula: $C_{28}H_{32}N_{10}O$.
Melting point: 236° C.

$^1$H NMR (DMSO-d$_6$): 2.99 (t, 2H, n-propyl CH$_2$); 4.02 (s, 2H, benzyl CH$_2$); 8.13 (s, 1H, H$_2$).

EXAMPLE 91

5,7-Dipropyl-6-[(2'-(1H-tetrazol-5-yl)biphenyl-4-yl)methyl]-1,2,4-triazolo[1,5-a]-pyrimidine Formula (I):
R$_1$=n-propyl, R$_2$=n-propyl, X=N, Y=CH,

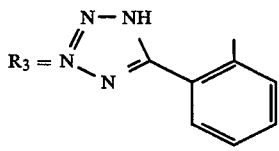

Empirical formula: C$_{25}$H$_{26}$N$_8$.
Melting point: 226° C.
$^1$H NMR (DMSO-d$_6$): 2.66 (t, 2H, n-propyl CH$_2$); 3.15 (t, 2H, n-propyl CH$_2$); 4.14 (s, 2H, benzyl CH$_2$); 8.26 (s, 1H, H$_2$).

EXAMPLE 92

7-Propyl-6-[(2'-(1H-tetrazol-5-yl)biphenyl-4-yl)methyl]-1,2,4-triazolo[1,5-a]pyrimidine Formula (I):
R$_1$=n-propyl, R$_2$=H, X=N,

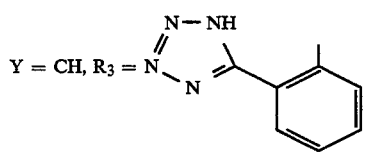

Empirical formula: C$_{22}$H$_{20}$N$_8$.
Melting point: 238° C.
$^1$H NMR (DMSO-d$_6$): 3.16 (t, 2H, n-propyl CH$_2$); 4.21 (s, 2H, benzyl CH$_2$); 8.65 (s, 1H); 8.82 (s, 1H).

EXAMPLE 93

7-Benzyloxymethyl-5-hydroxy-6-[(2'-(1H-tetrazol-5-yl)biphenyl-4-yl)methyl]-1,2,4-triazolo[1,5-a]pyrimidine

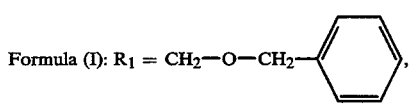

R$_2$ = OH, X = N, Y = CH,

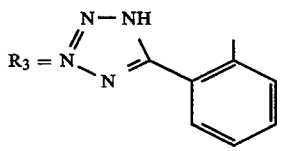

Empirical formula: C$_{27}$H$_{22}$N$_8$O$_2$.
Melting point: 270°-5° C. (decomposition).
$^1$H NMR (DMSO-d$_6$): 3.86 (s, 2H, benzyl CH$_2$); 4.62 (s, 2H, O-CH$_2$); 4.88 (s, 2H, O-CH$_2$); 8.11 (s, 1H, H$_2$).

EXAMPLE 94

5-(Piperidin-1-yl)-7-propyl-6-[(2'-(1H-tetrazol-5-yl)biphenyl-4-yl)methyl]-1,2,4-triazolo[1,5-a]pyrimidine Formula (I): R$_1$ = n-propyl, R$_2$ = N

X = N, Y = CH,

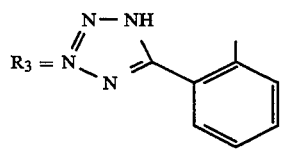

Empirical formula: C$_{27}$H$_{29}$N$_9$.
Melting point: 266° C.
$^1$H NMR (DMSO-d$_6$): 2.88 (t, 2H, n-propyl CH$_2$); 4.09 (s, 2H, benzyl CH$_2$); 8.35 (s, 1H, H$_2$).

EXAMPLE 95

[7-Propyl-6-[(2'-(1H-tetrazol-5-yl)biphenyl-4-yl)methyl]-1,2,4-triazolo[1,5-a]-pyrimidin-5-yl]2-methoxyethyl ether Formula (I):
R$_1$=n-propyl,
R$_2$=O-CH$_2$-CH$_2$-O-CH$_3$, X=N,

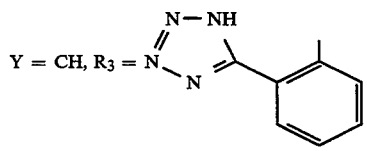

Empirical formula: C$_{25}$H$_{26}$N$_8$O$_2$.
Melting point: 224° C.
$^1$H NMR (DMSO-d$_6$): 3.14 (t, 2H, n-propyl CH$_2$); 4.04 (s, 2H, benzyl CH$_2$); 8.41 (s, 1H, H$_2$).

EXAMPLE 96

5-Chloro-7-propyl-6-[(2'-(1H-tetrazol-5-yl)biphenyl-4-yl)methyl]-1,2,4-triazolo-[1,5-a]pyrimidine Formula (I):
R$_1$=n-propyl, R$_2$=Cl, X=N,

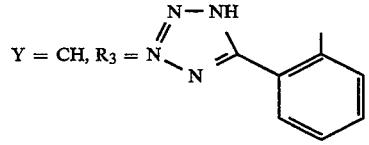

Obtained by diazotization of the derivative of Example 77 and treatment of the diazonium salt with cuprous chloride according to the classical Sandmeyer reaction.

EXAMPLE 97

6-[(2'-Aminocarbonylbiphenyl-4-yl)methyl]-5-hydroxy-7-propyl-1,2,4-triazolo[4,3-a]-pyrimidine Formula (I):
R$_1$=n-propyl, R$_2$=OH,

X=CH, Y=N,

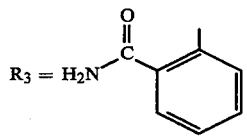

2 g of the compound of Example 20 d) in 200 ml of 1N NaOH are refluxed for 4 h. The mixture is concentrated under vacuum and the concentrate is acidified with 200 ml of 1N HCl. The crystals obtained are purified by recrystallization from 2-methoxyethanol to give 1.6 g of 6-[(2'-aminocarbonylbiphenyl-4-yl)methyl]-5-hydroxy-7-propyl-1,2,4-triazolo[4,3-a]pyrimidine.

Empirical formula: $C_{22}H_{21}N_5O_2$.

Melting point: 258° C.

$^1$H NMR (DMSO-d$_6$): 2.61 (t, 2H, n-propyl CH$_2$); 3.9 (s, 2H, benzyl CH$_2$); 9 (s, 1H, H$_3$).

EXAMPLE 98

6-[(2'-Carboxybiphenyl-4-yl)methyl]-5-hydroxy-7-propyl-1,2,4-triazolo[1,5-a]-pyrimidine Formula (I):
R$_1$=n-propyl, R$_2$=OH,
X=N, Y=CH,

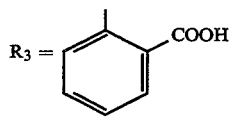

A mixture of 9.4 g of the product obtained in Example 97, 200 ml of ethylene glycol and 20 ml of concentrated NaOH is refluxed for 10 h. The ethylene glycol is distilled, 200 ml of water are added and the mixture is acidified with a solution of HCl. The crystals obtained are purified by recrystallization from 2-methoxyethanol to give 5.8 g of 6-[(2'-carboxybiphenyl-4-yl)methyl]-5-hydroxy-7-propyl-1,2,4-triazolo[1,5-a]-pyrimidine.

Empirical formula: $C_{22}H_{20}N_4O_3$.

Melting point: 265° C.

$^1$H NMR (DMSO-d$_6$): 2.96 (t, 2H, n-propyl CH$_2$); 3.92 (s, 2H, benzyl CH$_2$); 8.12 (s, 1H, H$_2$).

The compound of Example 99 was prepared by the procedure of Example 23.

EXAMPLE 99

6-[4-(5-Bromo-3-cyano-2-furyl)benzyl]-5-hydroxy-7-propyl-1,2,4-triazolo[1,5-a]-pyrimidine Formula (VIIb):
R'$_1$=n-propyl, X=N, Y=CH, R$_{10}$=OH,

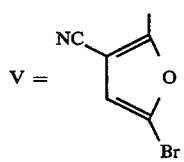

Melting point: 262° C.

EXAMPLE 100

6-[(2'-Cyanobiphenyl-4-yl)methyl]-5-hydroxy-7-hydroxymethyl-1,2,4-triazolo-[1,5-a]pyrimidine Formula (VIIb):
R'$_1$=CH$_2$OH, X=N,
Y=CH, R$_{10}$=OH,

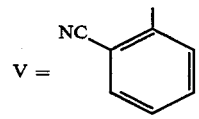

A solution of 9 g of the compounds prepared in Example 43 in 360 ml of acetic acid is reduced by catalytic hydrogenation in the presence of 1.8 g of 5% palladium-on-charcoal. The reaction is carried out at atmospheric pressure and at 50° C. The catalyst is filtered off on Célite 545 and washed with acetic acid and the filtrate is concentrated and then purified by chromatography on silica gel (eluent: chloroform 95%/methanol 5%) to give 4.5 g of the starting material and 2.2 g of 6-[(2'-cyanobiphenyl-4-yl)methyl]-5-hydroxy-7-hydroxymethyl-1,2,4-triazolo[1,5-a]pyrimidine.

Melting point: 262° C.

This same compound can also be obtained by reaction with BBr$_3$ in chloroform.

The following derivatives of Examples 101 and 102 were prepared by the procedure of Example 63.

EXAMPLE 101

5-Hydroxy-7-hydroxymethyl-6-[(2'-(1H-tetrazol-5-yl)biphenyl-4-yl)methyl]-1,2,4-triazolo[1,5-a]pyrimidine Formula (I):
R$_1$=CH$_2$OH, R$_2$=OH, X=N,

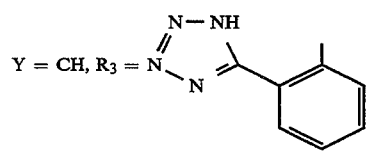

Empirical formula: $C_{20}H_{15}N_5O_2$.

Melting point: >360° C. (decomposition).

$^1$H NMR (DMSO-d$_6$): 3.93 (s, 2H, benzyl CH$_2$); 4.82 (s, 2H, CH$_2$-O); 8.06 (s, 1H, H$_2$).

EXAMPLE 102

6-[4-[5-Bromo-3-(1H-tetrazol-5-yl)-2-furyl]benzyl]-5-hydroxy-7-propyl-1,2,4-triazolo[1,5-a]pyrimidine Formula (I):
R$_1$=n-propyl, R$_2$=OH,
X=N, Y=CH,

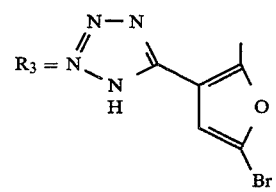

Empirical formula: $C_{20}H_{17}BrN_8O_2$.

Melting point: >360° C.

$^1$H NMR (DMSO-d$_6$): 2.93 (t, 2H, n-propyl CH$_2$); 3.92 (s, 2H, benzyl CH$_2$); 6.9 (s, 1H, furan proton); 8.03 (s, 1H, H$_2$).

PHARMACOLOGY

A. Study Of the adrenal angiotensin II receptors

I. Principle

The affinity of the products of the Examples for the angiotensin II receptors is evaluated by the technique of displacing a radioligand specifically bound to rat adrenal angiotensin II receptors.

II. Procedure

An aliquot of a rat adrenal gland homogenate incubates in the presence of a single concentration of [$^{125}$I]-SIAII (Sar$^1$, Tyr$^4$, Ile$^8$-angiotensin II), which is an angiotensin II receptor antagonist, and two concentrations of competing agents (10$^{-5}$M, 10$^{-7}$M) for 60 min at 25° C.

The reaction is completed by the addition of a buffer, followed by rapid filtration through glasspaper filters. The non-specific binding is determined in the presence of angiotensin II.

III. Expression of the results

The results are expressed, for the concentrations tested, as the percentage displacement of the radioligand specifically bound to the adrenal angiotensin II receptors.

IV. Results

| Product of | % displacement of the labeled ligand | |
|---|---|---|
| | 1E-5M | 1E-7M |
| Example 62 | 65 | 52 |
| Example 63 | 61 | 52 |
| Example 65 | 63 | 47 |
| Example 68 | 69 | 59 |
| Example 69 | 69 | 19 |
| Example 75 | 61 | 60 |
| Example 76 | 63 | 28 |
| Example 77 | 63 | 31 |
| Example 79 | 58 | 26 |
| Example 82 | 58 | 11 |

B. Measurement of the inhibition of the cell proliferation induced by growth factors (example: Platelet-Derived Growth Factor, or PDGF) in rat aorta smooth muscle cells I. Principle The inhibition of the cell proliferation induced by a growth factor (example: PDGF) is evaluated by measuring the incorporation of $^3$H-thymidine in rat aorta smooth muscle cells (VSMC).

II. Procedure

The VSMC are cultivated at 37° C. in 5% CO$_2$ until subconfluence is reached, and are then placed for 24 hours at rest in a serum-poor medium. They are subsequently pretreated for one hour with the test molecule (10$^{-4}$M) and then stimulated for 22 hours with a growth factor (example: PDGF). $^3$H-Thymidine is incorporated during the last 4 hours. All these steps are performed at 37° C. in 5% CO$_2$.

The reaction is terminated by sucking off the reaction medium, detaching the cells and then filtering the lyzed cells through glassfiber filters.

III. Expression of the results

The results are expressed as the percentage inhibition of the stimulation of incorporation of $^3$H-thymidine due to the action of the growth factor.

IV. Results

| Product of | % inhibition of the incorporation of $^3$H-thymidine induced by PDGF 1E-4M |
|---|---|
| Example 69 | 100 |

TOXICOLOGY

The products of the Examples described have an excellent tolerance after oral administration.

Their 50% lethal dose in rats was found to be greater than 300 mg/kg.

CONCLUSION

The products of the Examples described have a good affinity for the angiotensin II receptors. In this respect they may be used beneficially for the various pathological conditions in which angiotensin II is involved, in particular for the treatment of arterial hypertension and cardiac insufficiency, in dosages of 1 to 400 mg by oral administration and of 0.01 to 50 mg by intravenous administration, in one or more dosage units per day. Furthermore, some of the compounds also have an antiproliferative activity and in this respect are of potential value in the treatment of proliferative diseases such as atherosclerosis.

What is claimed is:

1. A triazolopyrimidine compound of formula (I):

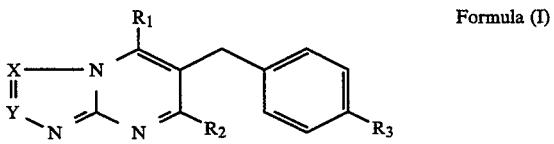

Formula (I)

in which:
one of the radicals R$_1$ and R$_2$ is
  a lower alkyl radical having 1 to 6 carbon atoms;
  an ether radical of the formula —(CH$_2$)$_p$OR, in which p is an integer from 1 to 6 and R is a lower alkyl radical having 1 to 6 carbon atoms or a benzyl radical; or
  an alcohol radical of the formula —(CH$_2$)$_p$OH, in which p is as defined above; and
the other radical R$_1$ or R$_2$ is
  the hydrogen atom;
  a halogen atom;
  a lower alkyl radical having 1 to 6 carbon atoms; or
  a radical selected from the group comprising the radicals N$_3$, OR$_4$, SR$_4$, NR$_5$R$_6$ and NH(CH$_2$)$_n$—NR$_5$R$_6$, in which:
R$_4$ is
  the hydrogen atom;
  a lower alkyl radical having 1 to 6 carbon atoms or a C$_3$–C$_7$-cycloalkyl radical;
  a radical (CH$_2$)$_m$—COOR', m being an integer from 1 to 4 and R' being the hydrogen atom or a lower alkyl radical having 1 to 6 carbon atoms; or
  a radical (CH$_2$)$_m$-O-R', m and R' being as defined above;
R$_5$ and R$_6$, which are identical or different, are
  the hydrogen atom; or a lower alkyl radical having 1 to 6 carbon atoms or a $C_3-C_7$-cycloalkyl radical; or $R_5$ and $R_6$, taken together with the nitrogen atom to which they are attached, form a heterocycle selected from morpholine, pyrrolidine or piperidine; and n is an integer from 1 to 4;

X and Y, which are different, are
in one case the nitrogen atom; and
in the other case a group C-$R_7$, in which $R_7$ is the hydrogen atom;
a lower alkyl radical having 1 to 6 carbon atoms or a $C_3-C_7$-cycloalkyl radical;
a radical $(CH_2)_{n'}OH$, in which n' is an integer from 0 to 4;
a radical SR', R' being as defined above; or
a radical $NR_5R_6$, in which $R_5$ and $R_6$, which are identical or different, are the hydrogen atom, a lower alkyl radical having 1 to 6 carbon atoms or a $C_3-C_7$-cycloalkyl radical; and $R_3$ is a radical of the formula

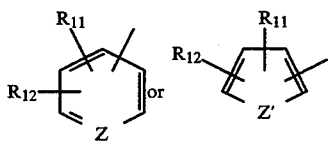

in which:
Z is CH or N or Z' is S or O;
$R_{11}$ is the hydrogen atom or a halogen atom; and
$R_{12}$ is a tetrazole radical, CN, COOH or $CONH_2$;
and its tautomeric forms and its pharmaceutically acceptable addition salts.

2. A compound according to claim 1 of formula (I) given above in which:
one of the radicals $R_1$ and $R_2$ is
a lower alkyl radical having 1 to 6 carbon atoms;
an ether radical of the formula $-(CH_2)_pOR$, in which p is an integer from 1 to 6 and R is a lower alkyl radical having 1 to 6 carbon atoms or a benzyl radical; or
an alcohol radical of the formula $-(CH_2)_pOH$, in which p is as defined above; and
the other radical $R_1$ or $R_2$ is
the hydrogen atom;
a halogen atom;
a lower alkyl radical having 1 to 6 carbon atoms; or
a radical selected from the group comprising the radicals $N_3$, $OR_4$, $SR_4$, $NR_5R_6$ and $NH(CH_2)_n-NR_5R_6$, in which:

$R_4$ is
the hydrogen atom; or
a radical $-(CH_2)_m-O-R'$ in which m is an integer from 1 to 4 and R' is a lower alkyl radical having 1 to 6 carbon atoms;

$R_5$ and $R_6$, which are identical or different, are
the hydrogen atom; or
a lower alkyl radical having 1 to 6 carbon atoms; or $R_5$ and $R_6$, taken together with the nitrogen atom to which they are attached, form a heterocycle selected from morpholine, pyrrolidine or piperidine; and n is an integer from 1 to 4;

X and Y, which are different, are
in one case the nitrogen atom; and
in the other case a group C—$R_7$ in which $R_7$ is the hydrogen atom;

a lower alkyl radical having 1 to 6 carbon atoms;
a radical $(CH_2)_{n'}OH$, in which n' is an integer from 0 to 4;
a radical SR', R' being as defined above; or
a radical $NR_5R_6$ in which $R_5$ and $R_6$, which are identical or different, are the hydrogen atom or a lower alkyl radical having 1 to 6 carbon atoms; and $R_3$ is one of the following radicals:

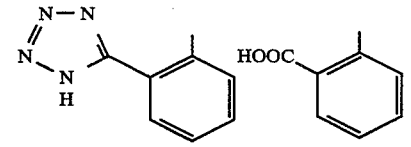

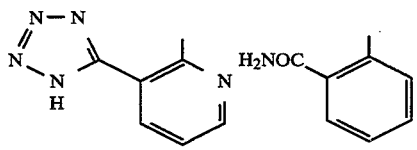

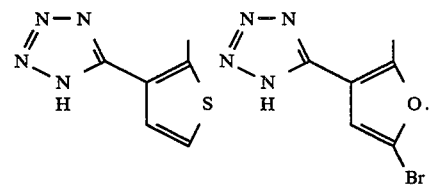

3. A compound according to claim 1 or claim 2 wherein $R_1$ is an n-propyl, n-butyl or N-diethylamino group.

4. A compound according to any one of claim 1 wherein $R_2$ is a hydroxyl, n-propyl or N-diethylamino group.

5. A compound according to claim 1 wherein $R_3$ is a 2-(1H-tetrazol-5-yl)phenyl group.

6. A compound according to claim 1 wherein X is the nitrogen atom.

7. A compound according to claim 1 wherein Y is the group CH, C—$CH_3$ or C—$NH_2$.

8. A compound according to claim 1 or claim 2 wherein $R_1$ is a lower alkyl radical having 1 to 6 carbon atoms, $R_2$ is a hydroxyl group, $R_3$ is a 2-(1H-tetrazol-5-yl)phenyl group, X is the nitrogen atom and Y is the group CH or C—$CH_3$.

9. A compound according to claim 1 or claim 2 which is the compound 5-hydroxy-7-propyl-6-[(2'-(1H-tetrazol-5-yl)biphenyl-4-yl)methyl]-1,2,4-triazolo[1,5a]-pyrimidine:

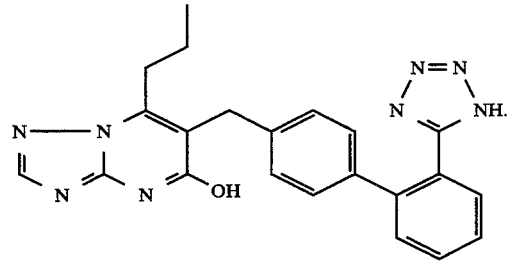

10. A compound according to claim 1 or claim 2 which is selected from the compounds of the formulae

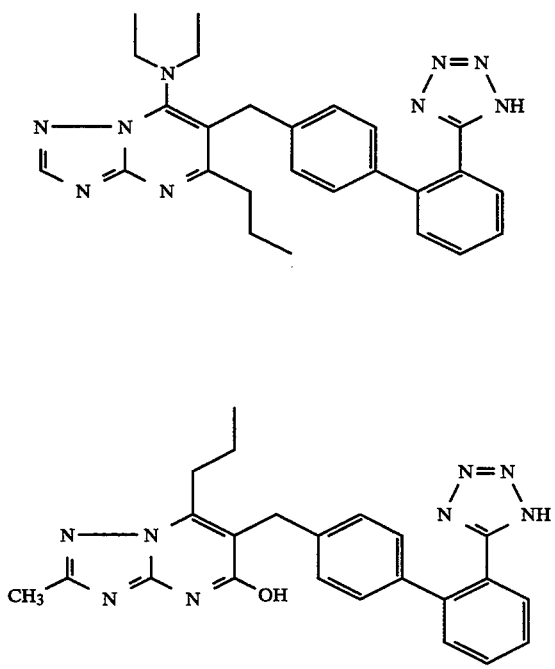

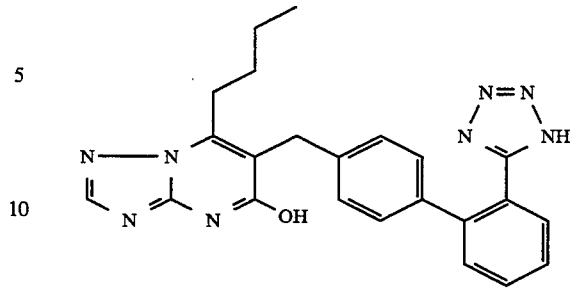

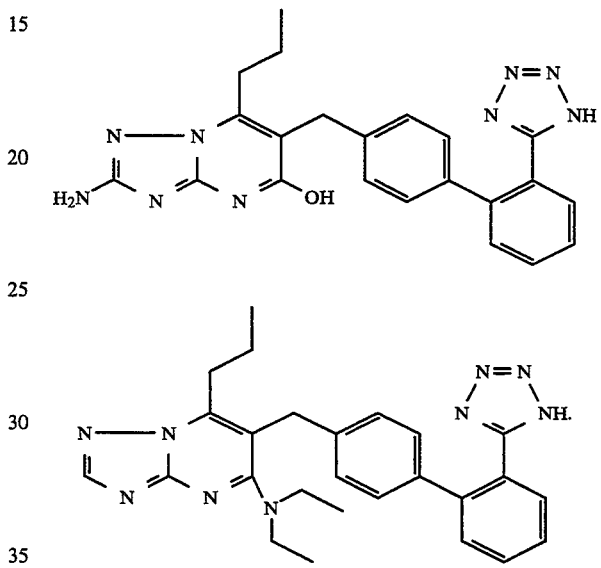

11. Pharmaceutical composition which comprises a pharmaceutically effective amount of at least one compound of formula (I) as defined in claim 1 or a pharmaceutically acceptable addition salt thereof, incorporated in a pharmaceutically acceptable excipient vehicle or carrier.

* * * * *

UNITED STATES PATENT AND TRADEMARK OFFICE
CERTIFICATE OF CORRECTION

PATENT NO. : 5,387,747
DATED : February 7, 1995
INVENTOR(S) : Nicole Bru-Magniez et al.

It is certified that error appears in the above-indentified patent and that said Letters Patent is hereby corrected as shown below:

On the Cover Page, after Item No. [73], and after "[*] Notice: The portion of the term of this patent subsequent to" delete "May 31, 2011" and add -- July 27, 2010 --.

Signed and Sealed this

Sixth Day of June, 1995

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,387,747
DATED : February 7, 1995
INVENTOR(S) : Nicole Bru-Magniez et al.

It is certified that error appears in the above-indentified patent and that said Letters Patent is hereby corrected as shown below:

On the Cover Page, after Item No. [73], and after "[*] Notice: The portion of the term of this patent subsequent to" delete "July 27, 2010" which was inserted by an earlier Certificate of Correction and add --April 6, 2012--.

Signed and Sealed this

Twenty-third Day of April, 1996

*Attest:*

BRUCE LEHMAN

*Attesting Officer*     *Commissioner of Patents and Trademarks*